United States Patent
Sugimoto et al.

(10) Patent No.: US 8,343,205 B2
(45) Date of Patent: Jan. 1, 2013

(54) STENT DELIVERY SYSTEM

(75) Inventors: Ryota Sugimoto, Ashigarakami-gun (JP); Takashi Kitaoka, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 276 days.

(21) Appl. No.: 12/750,061

(22) Filed: Mar. 30, 2010

(65) Prior Publication Data
US 2010/0249896 A1 Sep. 30, 2010

(30) Foreign Application Priority Data
Mar. 31, 2009 (JP) .................................. 2009-87376

(51) Int. Cl.
*A61F 2/06* (2006.01)
(52) U.S. Cl. ..................................... 623/1.11
(58) Field of Classification Search .................. 606/108, 606/109, 191, 192, 194; 623/1.11, 1.23, 623/2.11
See application file for complete search history.

(56) References Cited

U.S. PATENT DOCUMENTS

| | | | | | |
|---|---|---|---|---|---|
| 4,830,003 | A | * | 5/1989 | Wolff et al. | 606/191 |
| 5,030,227 | A | * | 7/1991 | Rosenbluth et al. | 606/192 |
| 5,391,172 | A | * | 2/1995 | Williams et al. | 623/1.11 |
| 5,415,664 | A | * | 5/1995 | Pinchuk | 623/1.11 |
| 5,480,423 | A | * | 1/1996 | Ravenscroft et al. | 623/1.11 |
| 5,507,768 | A | * | 4/1996 | Lau et al. | 623/1.11 |
| 5,643,278 | A | * | 7/1997 | Wijay | 623/1.11 |
| 5,690,644 | A | * | 11/1997 | Yurek et al. | 623/1.11 |
| 5,733,325 | A | * | 3/1998 | Robinson et al. | 623/1.11 |
| 5,957,930 | A | * | 9/1999 | Vrba | 623/1.11 |
| 5,984,964 | A | * | 11/1999 | Roberts et al. | 623/1.11 |
| 5,989,280 | A | * | 11/1999 | Euteneuer et al. | 623/1.1 |
| 7,963,987 | B2 | * | 6/2011 | Melsheimer et al. | 623/1.11 |
| 2001/0049549 | A1 | * | 12/2001 | Boylan et al. | 623/1.11 |
| 2001/0056298 | A1 | | 12/2001 | Brown et al. | |
| 2006/0282149 | A1 | * | 12/2006 | Kao | 623/1.11 |
| 2007/0027521 | A1 | * | 2/2007 | Andreas et al. | 623/1.11 |
| 2007/0191864 | A1 | * | 8/2007 | Shumer | 606/108 |
| 2007/0191865 | A1 | * | 8/2007 | Pappas | 606/108 |
| 2008/0039919 | A1 | * | 2/2008 | Kaplan et al. | 623/1.11 |
| 2009/0048655 | A1 | * | 2/2009 | Jang | 623/1.11 |
| 2009/0326560 | A1 | * | 12/2009 | Lampropoulos et al. | 606/148 |
| 2012/0172969 | A1 | * | 7/2012 | Sugimoto et al. | 623/1.12 |

FOREIGN PATENT DOCUMENTS

| | | |
|---|---|---|
| JP | 11-505441 A | 5/1999 |
| JP | 2008-272374 A | 11/2008 |
| WO | WO 96/26689 A1 | 9/1996 |

* cited by examiner

*Primary Examiner* — Ryan Severson
*Assistant Examiner* — Jonathan W Miles
(74) *Attorney, Agent, or Firm* — Buchanan Ingersoll & Rooney PC

(57) ABSTRACT

A stent delivery system includes a stent formed in a substantially hollow cylindrical shape and compressed toward its center axis when inserted in vivo, with the stent being capable of restoring its pre-compression shape through outward expansion when left indwelling in vivo. The stent delivery system also includes an inner tube possessing a guide wire lumen, and a stent accommodating tube having a distal portion accommodating the stent. The stent is disposed as to cover a distal portion of the inner tube, and the stent is adapted to be exposed by moving the stent accommodating tube toward the proximal side relative to the inner tube.

12 Claims, 22 Drawing Sheets

STENT DELIVERY SYSTEM

TECHNICAL FIELD

The disclosure here generally pertains to a medical device delivery system. More specifically, the disclosure here relates to a stent delivery system used for curing a lesioned part such as plaque, a stenosed lesion, an occluded lesion, etc. existing in a living lumen such as a blood vessel, bile duct, trachea, esophagus, urethra, etc.

BACKGROUND DISCUSSION

Diseases related to the cardiovascular area includes quantitative abnormalities of the degree of progress of lesion due to arteriosclerotic hypertrophy, and abnormalities such that a fibrous membrane at the surface of atheroma called vulnerable plaque which is thin and brittle comes to rupture to cause thrombus, bleeding, stenosis or occlusion, leading to crisis of stenocardia, myocardial infarction or cerebral infarction.

Vulnerable plaque cannot be checked under a radiography. Therefore, to check vulnerable plaque, the intended blood vessel is determined by use of OCT (optical coherence tomography) or the like. Using OCT or the like, the location of the vulnerable plaque is determined using data on the distance between the vulnerable plaque and a nearest bifurcated blood vessel, the distance between the vulnerable plaque and a stent previously left indwelling, or the like.

To cure a lesion such as plaque, a stenosed lesion, an occluded lesion, etc. generated in a blood vessel or other lumen in vivo, a stent is left indwelling in the lesion to maintain patency of the lumen.

Since the stent is inserted in vivo from the exterior, the stent is small in diameter at the time of insertion. The stent is enlarged in diameter through expansion in the stenosed lesion or the occluded lesion and maintains patency of the lumen.

The stents that are generally used include hollow cylindrical stents obtained by processing metallic wire or metallic pipe. The stent is mounted on a catheter or the like while in a reduced diametrical size, and is then inserted in vivo, and is expanded in a target lesion by a known method to come into close contact with and be fixed on the inner wall of the target lesion (lumen), thereby maintaining patency of the lumen. The stents are classified into self-expandable stents and balloon-expandable stents according to function and method of indwelling. A balloon-expandable stent is a stent which itself does not have an expanding function. Instead, after the stent mounted on a balloon is inserted into a target lesion, the balloon is dilated so that the stent is expanded (plastically deformed) by the expanding (dilating) force of the balloon to come into close contact with and be fixed on the inner surface of the target lumen. This type of stent needs the just-mentioned stent-expanding work. On the other hand, a self-expandable stent is a stent which itself is provided with an expanding function. This type of stent is inserted in vivo in the state of being compressed to a smaller diametrical size, and is released in a target lesion from the compression to return into its initial expanded state and to come into close contact with and be fixed on the inner wall of the target lumen, thereby maintaining patency of the lumen.

The purpose of indwelling a stent at present is for returning a stenosed blood vessel into its original patency, and mainly for preventing restenosis which might otherwise occur after such a procedure as PTCA is conducted. In recent years, stents have come to be used for ameliorating a lesion (plaque) which will highly probably become a stenosed region.

The self-expandable stents are mostly used in peripheral regions such as blood vessels in femoral and carotid arteries, and include, for example, those having a form as shown in JP-T-H11-505441.

Another self-expandable stent is shown in Japanese Patent Laid-Open No. 2008-272374. A stent delivery system 1 according to Japanese Patent Laid-Open No. 2008-272374 includes a distal-side tube 2, a proximal-side tube 4 fixed to a proximal portion of the tube 2, a stent accommodating tubular member 5 which can be slid in the proximal direction, a self-expandable stent 3 accommodated in the stent accommodating tubular member 5, and a pulling traction wire 6 for moving the stent accommodating tubular member 5 toward the proximal side. The stent accommodating tubular member 5 is moved on the outer surface of a fixed tube 8 toward the proximal side by pulling the wire 6. The stent accommodating tubular member 5 has a tubular proximal member 54 made of a hard material which is fixed to the proximal end of the stent accommodating tubular member 5 and has an inner surface making contact with the outer surface of the fixed tube 8 when the stent accommodating tubular member 5 is moved toward the proximal side.

In the case where a stent delivery system which uses a self-expandable stent proposed in JP-T-H11-505441 and Japanese Patent Laid-Open No. 2008-272374 is used and the stent is positioned in the lesion (e.g., plaque forming), the position of a vulnerable plaque is determined, before insertion of the delivery system, by way of the distance between the vulnerable plaque and an indicator such as the nearest bifurcated blood vessel, a stent previously left indwelling, etc. by use of the above-mentioned OCT.

Then, the stent accommodating part of the delivery system is inserted in the determined lesion, and thereafter the stent is discharged, whereby the stent is indwelled in the lesion.

However, the self-expandable stent has difficulties in that its initial positioning for indwelling must be conducted accurately, since the stent restores its original shape by its own expanding force once it is discharged. In addition, in many cases, the self-expandable stent itself is not clearly confirmed under radiography. Besides, the plaque forming lesion cannot be checked under radiography while the delivery system is set indwelling in the lesion.

SUMMARY

The stent delivery system disclosed here allows a self-expandable stent to be relatively assuredly indwelled in a lesion that is difficult to check under radiography. This is accomplished using a method in which the distance between the lesion and an indicator such as a nearest bifurcated blood vessel, a stent previously left indwelling, etc. is determined by the OCT or the like, and the stent is set indwelling by utilizing the thus determined distance.

A stent delivery system disclosed here includes a stent accommodating tube possessing a distal end portion, an inner tube positioned inside the stent accommodating tube, with the inner tube possessing a guide wire lumen extending along at least a portion of a longitudinal extent of the inner tube and being configured to receive a guide wire, and a stent possessing a hollow cylindrical shape and having a central axis. The stent is removably positioned in the stent accommodating tube and covers a distal end portion of the inner tube, with the stent being exposable outside the stent accommodating tube by moving the stent accommodating tube toward the proximal side relative to the inner tube. The stent is configured to be compressed toward its central axis when positioned in the stent accommodating tube and to outwardly expand towards its pre-compression shape after being exposed outside the stent accommodating tube and left indwelling in vivo. The inner tube comprises a radiopaque indication region extending at least over a predetermined length of the inner tube in a proximal direction from the proximal end of the stent. The radiopaque region comprises a plurality of radiopaque markers, with a distance between adjacent radiopaque markers being the same to permit distance determination.

The radiopaque indication region is preferably provided over a distance of more than 5 mm from the position corresponding to the proximal end of the stent.

The plurality of radiopaque markers are preferably scale-like radiopaque markers provided at equal intervals.

The scale-like radiopaque markers preferably include a plurality of main scales and auxiliary scales, the latter of which are provided between the plurality of main scales and are lower in radiopacity than the main scales.

The radiopaque indication region has a starting point at a position corresponding to the distal end or a middle portion of the stent, and extends toward the proximal side over a predetermined length.

The stent delivery system can also include a stent proximal end fixing linear member of which one end portion and the other end portion are fixed to the inner tube and an intermediate portion is moored to a proximal end of the stent, and a rupture portion for rupturing the stent proximal fixing linear member so as to release the mooring of the stent.

The stent is provided in its proximal end with a plurality of small holes permitting the stent proximal end fixing linear member to pass therethrough, the small holes being provided in a substantially annular fashion, and the intermediate portion of the stent proximal end fixing linear member is passed through the plurality of small holes in an annular fashion.

The stent can be provided with a plurality of proximal end direction bent portions located at a proximal end thereof, and the intermediate portion of the stent proximal end fixing linear member is passed through the plurality of proximal end direction bent portions in an annular fashion.

The inner tube includes a distal-side tube having the guide wire lumen, and an inner tube body having a distal portion fixed to the proximal side of the distal-side tube, and the rupture portion is provided at the distal portion of the inner tube body.

The stent proximal end fixing linear member is preferably a heat-rupturing stent proximal end fixing linear member, and the rupture portion is a heat rupture portion.

The inner tube has an opening communicating with the guide wire lumen on the proximal side relative to the stent accommodating portion of the stent accommodating tube, and the radiopaque indication region extends to the vicinity of the opening.

The stent can be again accommodated into the stent accommodating tube until the stent proximal end fixing linear member is ruptured and the mooring of the stent is thereby released.

The stent delivery system disclosed here includes a stent formed in a substantially hollow cylindrical shape and compressed toward its center axis when inserted in vivo, the stent being capable of restoring its pre-compression shape through expanding outwards when left indwelling in vivo, an inner tube having a guide wire lumen, and a stent accommodating tube accommodating the stent in a distal portion thereof, the stent being so disposed as to cover a distal portion of the inner tube, and the stent being exposable by moving the stent accommodating tube toward the proximal side relative to the inner tube, wherein the inner tube has a radiopaque indication region extending at least over a predetermined length toward the proximal side from a position corresponding to the proximal end of the stent, and a distance indicating function offered by a plurality of radiopaque markers arranged to be mutually spaced at a predetermined interval is provided in the radiopaque indication region.

The distance between the lesion which is difficult to check under radiography and an indicator such as a bifurcated blood vessel which is on the proximal side in the insertion direction of the delivery system relative to a proximal end of the lesion and is nearest to the proximal end, a stent previously left indwelling, a calcified lesion, another stenosed lesion, a coronary artery inlet, etc. is determined by use of, for example, the OCT or the like. Then, in the delivery system, a proximal end of the stent of the delivery system inserted into a blood vessel can be so disposed as to be spaced from the indicator by a distance equal to the distance between the proximal end of the lesion and the indicator, by use of the distance indicating function of the radiopaque indication region. The result is that it is possible to assuredly dispose the stent at the lesion, and by maintaining this condition and moving the stent accommodating tube toward the proximal side, it is possible to assuredly set the stent indwelling in the lesion.

In addition, the delivery system disclosed here is effective also in putting a stent indwelling in a stenosed lesion which is a lesion capable of being checked under radiography or the like. The delivery system enables the stent to be reliably disposed in the stenosed lesion which is a lesion capable of being checked under radiography or the like, by a method wherein the distance between a proximal end of the stenosed lesion and an indicator such as a bifurcated blood vessel which is on the proximal side in the insertion direction of the delivery system relative to the proximal end and is nearest to the proximal end, a stent previously left indwelling, etc. is preliminarily measured, and a proximal end of the stent of the delivery system inserted in the blood vessel is so disposed as to be spaced from the indicator by the preliminarily measured distance by use of the distance indicating function of the radiopaque indication region. Then, by maintaining this condition and moving the stent accommodating tube toward the proximal side, the stent can be assuredly set indwelling in the stenosed lesion.

According to another aspect, a stent delivery system includes a stent accommodating tube possessing a distal end portion, and an inner tube positioned inside the stent accommodating tube in a manner permitting the stent accommodating tube to be moved proximally relative to the inner tube, wherein the inner tube possesses a guide wire lumen extending along at least a portion of a longitudinal extent of the inner tube and being configured to receive a guide wire, and with the guide wire lumen having opposite ends opening outside the stent accommodating tube. The system also includes a hollow cylindrically shaped stent which possesses a proximal end, with the stent being removably positioned in the stent accommodating tube in a configuration in which the stent is inwardly compressed. The stent encircles a distal end portion of the inner tube, and is exposable outside the stent accommodating tube by proximally moving the stent accommodating tube relative to the inner tube. The stent is configured to automatically expand outwardly after being exposed outside the stent accommodating tube and left indwelling in vivo. A plurality of radiopaque markers on the inner tube, with the radiopaque markers being spaced apart from one another along a longitudinal extent of the inner tube. The plurality of radiopaque markers comprises a first one of the radiopaque markers positioned at the proximal end of the stent and additional ones of the plurality of radiopaque markers being positioned proximally from the first radiopaque markers, wherein the first radiopaque marker is a distal-most radiopaque marker on the inner tube, and adjacent ones of the plurality of radiopaque markers are spaced apart from one another by a common distance to permit distance determination during use of the stent delivery system.

DETAILED DESCRIPTION

Figure 1:
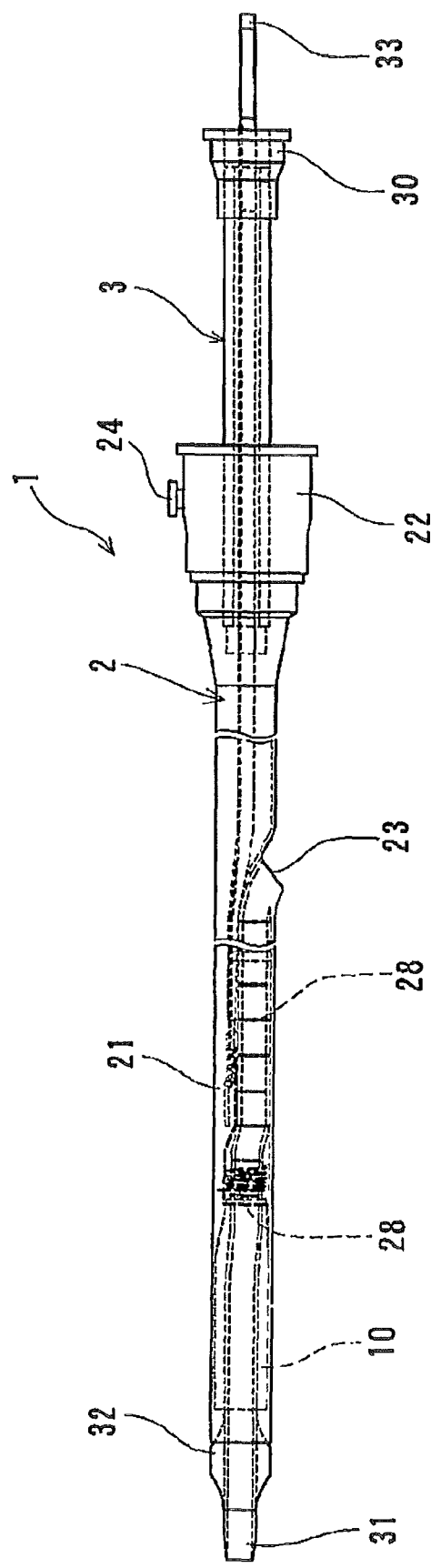
FIG. 1 is a side view of a stent delivery system according to an embodiment disclosed here.
Figure 2:
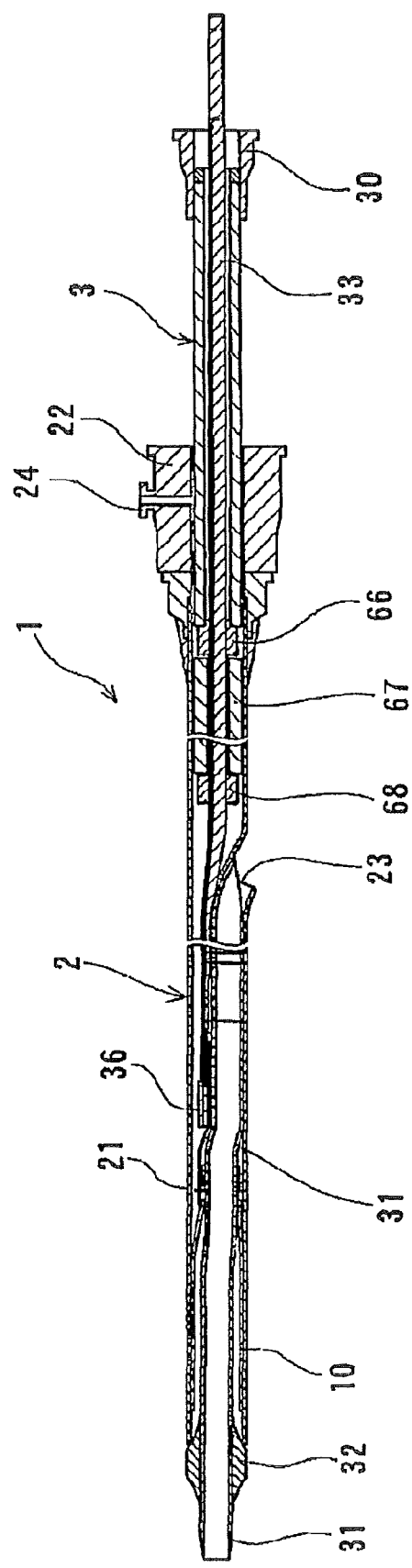
FIG. 2 is a longitudinal cross-sectional view of the delivery system shown in FIG. 1.
Figure 3:
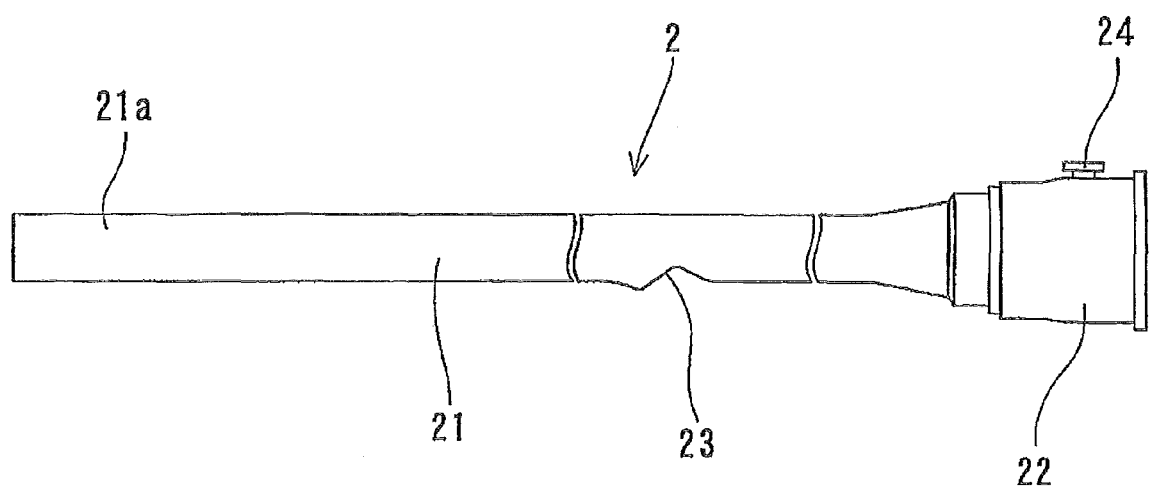
FIG. 3 is a side view of a portion of the stent accommodating tube (sheath) of the delivery system shown in FIG. 1.

The stent delivery system disclosed here is described below with reference to the accompanying drawings. The stent delivery system 1 according to one disclosed embodiment comprises a stent 10 formed in a substantially hollow cylindrical shape and compressed toward its center axis when inserted in vivo, with the stent 10 being capable of restoring its pre-compression shape through outward expansion when left indwelling in vivo. The stent delivery system 1 also includes an inner tube (shaft part) 3 having a guide wire lumen 61 (shown in FIG. 5), and a stent accommodating tube (sheath) 2 accommodating the stent 10 in the distal portion of the accommodating tube 2 so that the stent 10 covers a distal portion of the inner tube 3, and the stent 10 can be exposed by moving the stent accommodating tube 2 toward the proximal side (in the proximal direction) relative to the inner tube 3. The inner tube 3 has a radiopaque indication region extending proximally over at least a predetermined length from a position corresponding to the proximal end of the stent 10. A distance indicating function offered by a plurality of radiopaque markers 28 (28a, 28b) arranged so that they are mutually spaced at a predetermined interval (the same distance between adjacent markers) is provided in the radiopaque indication region.

In this disclosed and illustrated embodiment of the delivery system 1, the inner tube is composed of the shaft portion 3, and the stent accommodating tube is composed of the sheath 2.

Figure 4:
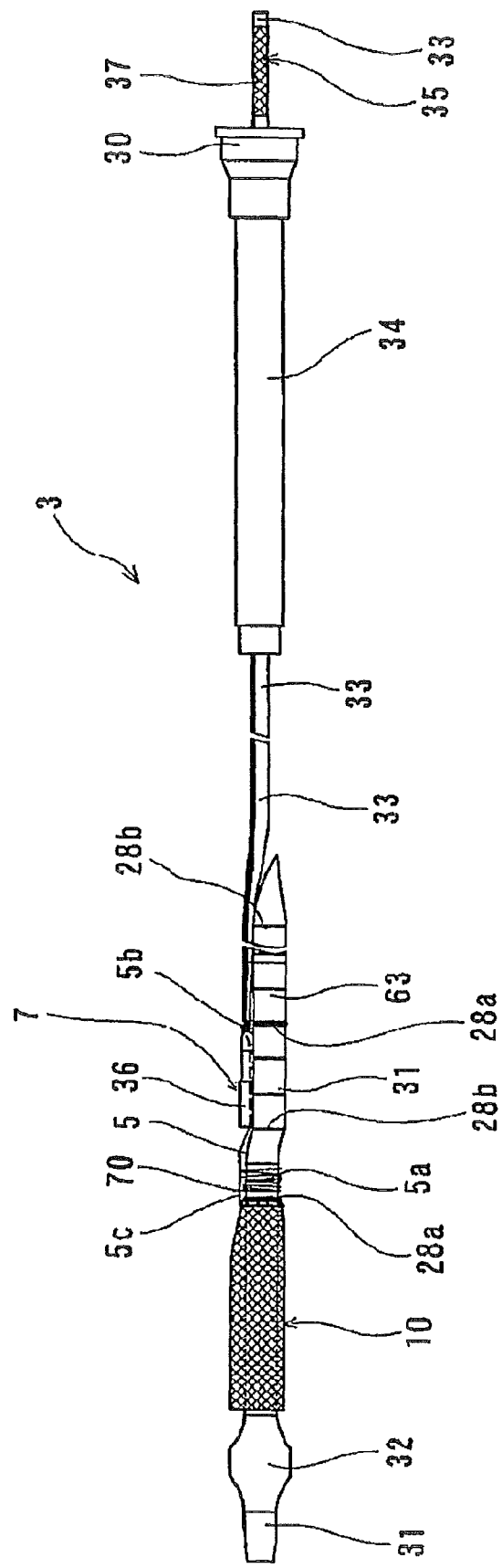
FIG. 4 is a side view of an inner tube of the delivery system shown in FIG. 1.
Figure 5:
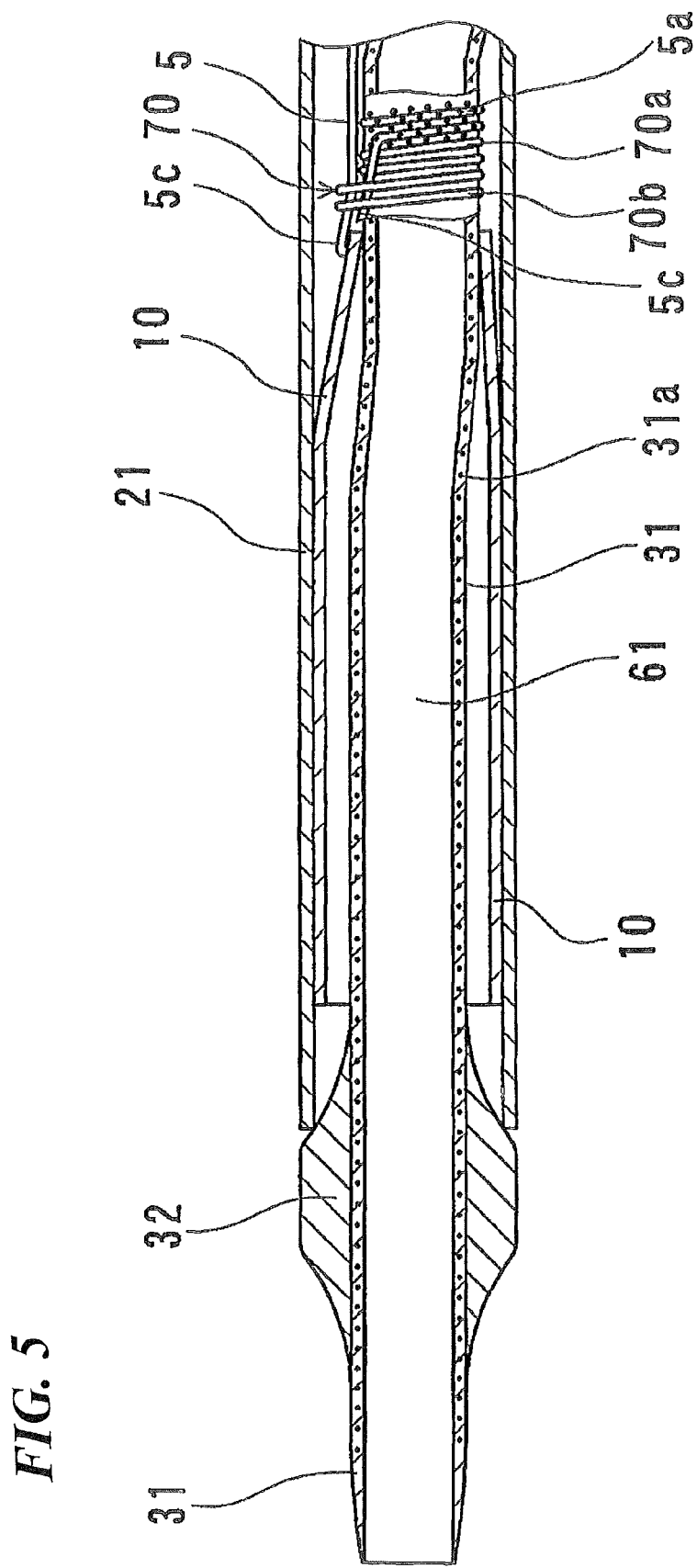
FIG. 5 is an enlarged longitudinal cross-sectional side view of the distal portion of the delivery system shown in FIG. 1.
Figure 6:
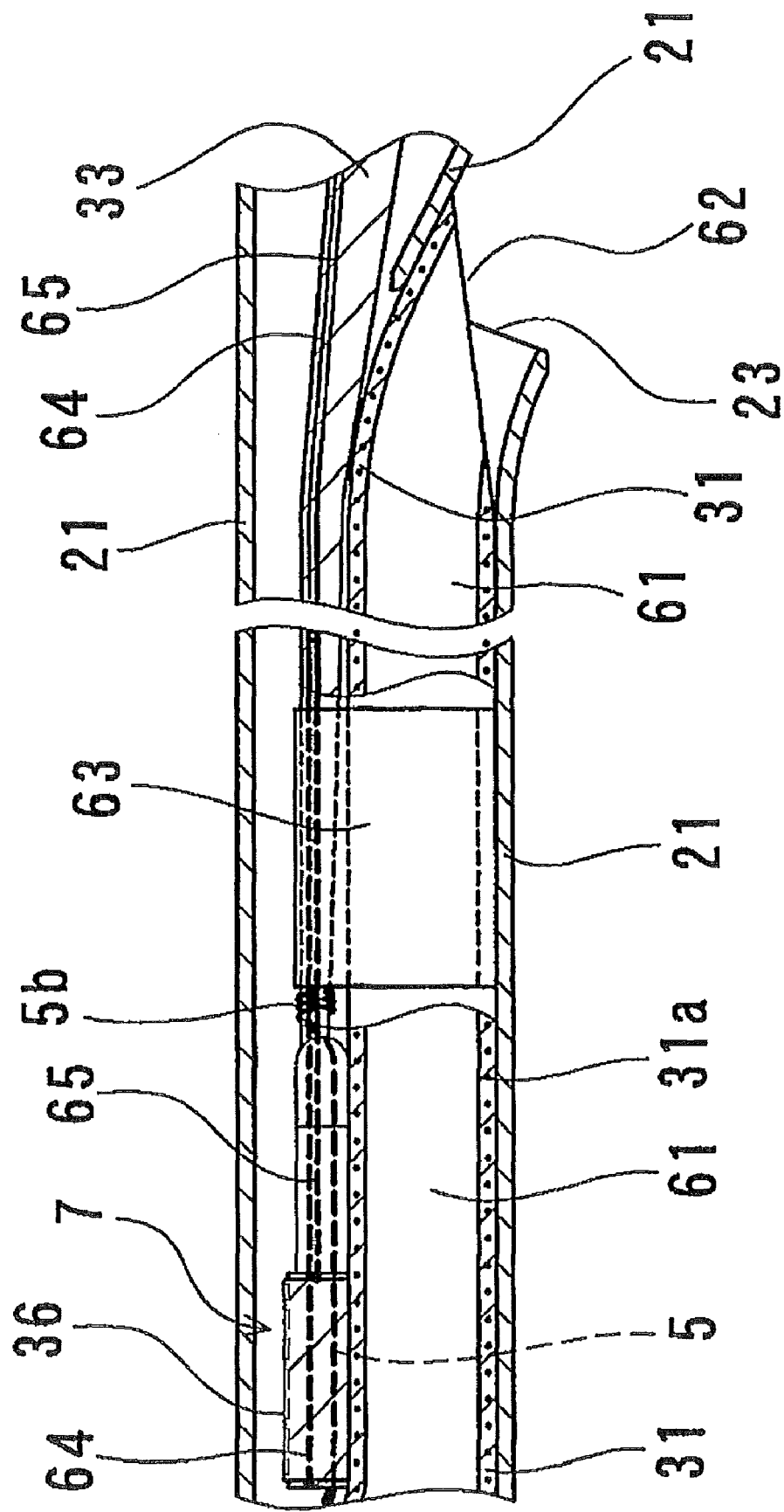
FIG. 6 is an enlarged longitudinal cross-sectional view of an intermediate portion of the delivery system shown in FIG. 1.

Referring to, for example, FIGS. 4-6, the delivery system 1 also includes a stent proximal end fixing linear (filamentous) member 5 having one end portion 5a and the other end portion 5b fixed to the shaft part 3 and having an intermediate portion 5c moored or fixed to the proximal end of the stent 10, and a rupture portion 7 for rupturing the stent proximal end fixing linear member 5 to release the mooring or fixation (securement) of the stent 10.

In addition, the delivery system 1 in the illustrated embodiment shown in the drawings includes the stent 10 which can restore its pre-compression shape through outward expansion when left indwelling in vivo, the sheath 2 accommodating the stent 10 in its distal portion, and the shaft part 3 for permitting the sheath 2 to cover slidably thereon and for discharging the stent 10 from the distal end of the sheath 2. The stent 10 has a distal end directed toward the distal side and a proximal end directed to the proximal side of the sheath 2. Further, the stent 10 does not have any free bent portion protruding toward the proximal side, except for the proximal end, and, by moving the sheath 2 after the distal end of the stent 10 is exposed from the sheath 2, the exposed distal end can again be accommodated into the sheath 2. The delivery system 1 has the guide wire lumen 61 which has one end opening at the distal end of the delivery system and has the other end opening on the proximal side relative to the stent accommodating portion of the sheath 2. The shaft 3 includes the stent proximal end fixing linear member 5 having one end portion 5a and the other end portion 5b fixed to the shaft part 3 and having the intermediate portion 5c moored or fixed to a proximal end of the stent 10, and the rupture portion 7 for rupturing the stent proximal end fixing linear member 5 to thereby release the mooring or fixation of the stent 10.

The delivery system 1 is composed of the stent 10, the sheath (stent accommodating tube) 2 accommodating the stent 10 in its distal portion, and the shaft part (inner tube) 3 permitting the sheath 2 to cover slidably thereon.

As shown in FIGS. 1 to 9, the sheath (stent accommodating tube) 2 includes a sheath tube 21, and a sheath hub 22 fixed to the proximal end of the sheath tube 21.

As shown in FIGS. 1 to 9, the sheath tube 21 is a tubular body which is open at its distal end and at its proximal end so that the sheath tube possesses open distal and proximal ends. The distal opening is a discharging port for the stent 10 when the stent 10 is indwelled at a lesion in a body lumen. Upon being discharged from the distal opening, the stent 10 is relieved from compression stress and expands, thereby restoring its pre-compression shape. A distal portion of the sheath tube 21 is a stent accommodating portion 21a in which is accommodated the stent 10. In addition, the sheath tube 21 has a side hole 23 on the proximal side relative to the stent accommodating portion 21a. The side hole 23 is for leading out a guide wire to the exterior.

The outside diameter of the sheath tube 21 is preferably about 0.5 to 4.0 mm, more preferably 0.8 to 2.0 mm. The inside diameter of the sheath tube 21 is preferably about 0.2 to 1.8 mm. The length of the sheath tube 21 is preferably 300 to 2500 mm, more preferably 300 to 2000 mm. Taking into account the physical properties required of the sheath tube (flexibility, hardness, strength, slidability, anti-kinking property, stretchability), preferable examples of the material forming the sheath tube 21 include polyethylene, polypropylene, nylon, polyethylene terephthalate, fluoropolymers such as PTFE, ETFE, etc. and, further, thermoplastic elastomers. The thermoplastic elastomer is appropriately selected from among nylon-based ones (e.g., polyamide elastomers), urethane-based ones (e.g., polyurethane elastomer), polyester-based ones (e.g., polyethylene terephthalate elastomer), and olefin-based ones (e.g., polyethylene elastomer, polypropylene elastomer).

Furthermore, the outer surface of the sheath 2 is preferably treated to show lubricity. Such a treatment may, for example, be conducted by a method wherein a hydrophilic polymer such as poly(2-hydroxyethyl methacrylate), polyhydroxyethyl acrylate, hydroxypropyl cellulose, methyl vinyl ether-maleic anhydride copolymer, polyethylene glycol, polyacrylamide, polyvinyl pyrrolidone, etc. is applied or fixed to the outer surface of the sheath 2. In addition, one of the hydrophilic polymers may be applied or fixed to the inner surface of the sheath tube 21, for enhancing slidability of the stent 10 and the shaft part 3 on the inner surface.

Figure 9:
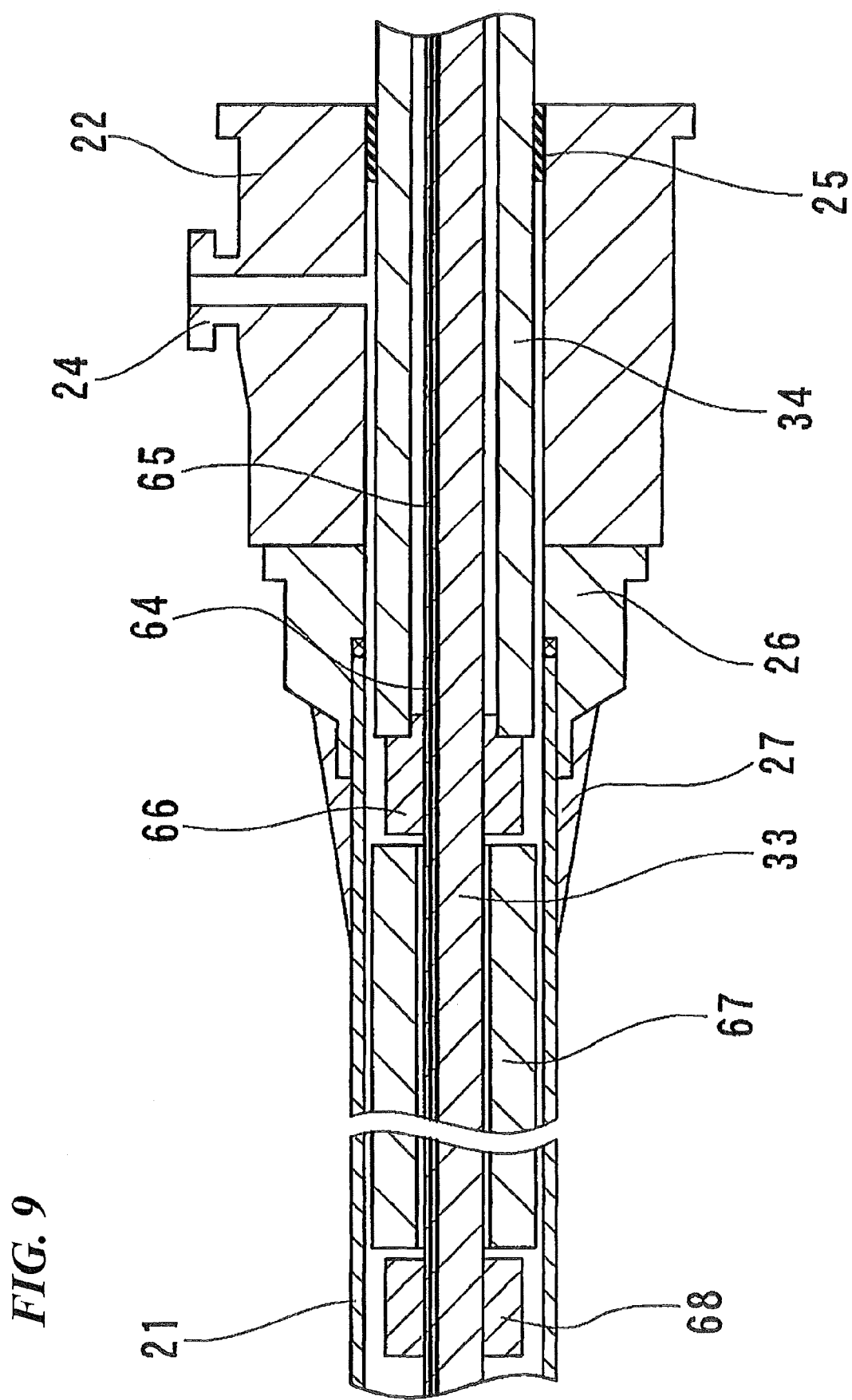
FIG. 9 is an enlarged longitudinal cross-sectional view of the proximal portion of the sheath of the delivery system shown in FIG. 1.

As shown in FIGS. 1-3 and 9, the sheath hub 22 is fixed to the proximal end of the sheath tube 21. As shown in FIG. 9, a seal member 25 is provided to hold the shaft part 3 in a slidable and liquid-tight manner. In addition, the sheath hub 22 is provided with a side port 24.

The material of the sheath hub 22 is preferably a hard or semi-hard material. Examples of the hard or semi-hard material include synthetic resins such as polycarbonate, polyolefins (e.g., polyethylene, polypropylene, ethylene-propylene copolymer), styrene resins [e.g., polystyrene, MS resins (methacrylate-styrene copolymer), MBS resin (methacrylate-butylene-styrene copolymer)], and metals such as stainless steels, aluminum, and aluminum alloys.

The materials used to fabricate the seal member 25, and an elastic ring 69 which will be described later, are preferably elastic materials. Examples of the elastic materials include rubbers such as synthetic rubbers, for example, urethane rubber, silicone rubber, butadiene rubber, etc. and natural rubbers such as latex rubber, etc., and synthetic resin elastomers such as olefin elastomers (e.g., polyethylene elastomer, polypropylene elastomer), polyamide elastomers, styrene elastomers (e.g., styrene-butadiene-styrene copolymer, styrene-isoprene-styrene copolymer, styrene-ethylenebutylene-styrene copolymer), polyurethane, urethane elastomer, fluororesin elastomer, etc.

As illustrated in FIG. 9, The distal portion of the sheath hub 22 is outfitted with reinforcement members 26, 27 which extend toward the distal side relative to the sheath hub's distal end.

As shown in FIGS. 1-10, the shaft part (inner tube) 3 includes a shaft body 33, a distal-side tube 31 at the distal end of the shaft body 33 and protruding from the distal end of the sheath 2, a shaft hub 30 fixed to the proximal end portion of the shaft body 33, a stent proximal end fixing linear member 5 fixed to the shaft body 33, and the rupture portion 7 in the shaft body 33 to effect rupturing of the stent proximal end fixing linear member 5.

In this embodiment, the stent proximal end fixing linear member 5 is a heat-rupturing stent proximal end fixing linear member, and the rupture portion 7 is a heat-rupturing portion. The rupture portion 7 is not limited to a heat-rupturing portion. The stent proximal end fixing linear member 5 and the rupture portion 7 may be members which are appropriately configured and constructed to be ruptured electrically, mechanically or by water pressure to disconnect the shaft part 3.

In this embodiment, the shaft part 3 has a guide wire lumen proximal opening which opens in a side portion on the proximal side relative to the stent accommodating portion of the sheath 2, and the sheath 2 has a sheath side port provided on the proximal side relative to the stent accommodating portion so that a guide wire can pass through the sheath side hole and the proximal opening.

As shown in FIG. 5, the distal-side tube 31 protrudes from the distal end of the sheath 2. That is, the distal-most end of the distal-side tube 31 extends distally beyond the distal-most end of the sheath 2. In addition, the distal-side tube 31 is provided with an outwardly projecting stopper 32 for inhibiting the sheath 2 from moving in the distal direction. The stopper 32 has an outer dimension larger than the portion of the distal-side tube 31 on both immediate sides of the stopper. A proximal portion of the distal-side tube 31 is curved, as shown in FIG. 6, to penetrate into (pass through) the side hole 23 of the sheath tube 21, to achieve releasable engagement. The outside diameter of the distal-side tube 31 is preferably 0.2 to 1.8 mm. A distal portion of the stopper 32 is preferably reduced in outer diameter toward the distal side as shown in FIG. 5. The outside diameter of the stopper 32 at its maximum diameter portion is preferably 0.5 to 4.0 mm. In addition, it is preferable that a proximal portion of the stopper 32 is also reduced in diameter toward the proximal side as shown in FIG. 5. The distal-side tube 31 has a guide wire lumen 61 extending from its distal end to its proximal end, and the position of a proximal opening 62 of the guide wire lumen 61 is preferably spaced from the distal end of the distal-side tube 31 toward the proximal side by 10 to 400 mm, more preferably 50 to 350 mm. The position of the proximal opening 62 is preferably spaced from the proximal end of the stent 10 (in other words, the proximal end of the stent accommodating portion) toward the proximal side by about 50 to 250 mm.

The inner tube 3 has a radiopaque indication region which extends at least over a predetermined length toward the proximal side relative to a position corresponding to the proximal end of the stent 10. A distance indicating function offered by a plurality of radiopaque markers 28a, 28b arranged to be mutually spaced at a predetermined interval is provided in the radiopaque indication region. That is, the radiopaque indication region includes a plurality of radiopaque markers 28a and a plurality of radiopaque markers 28b, with adjacent markers being spaced apart at equal intervals.

Figure 7:
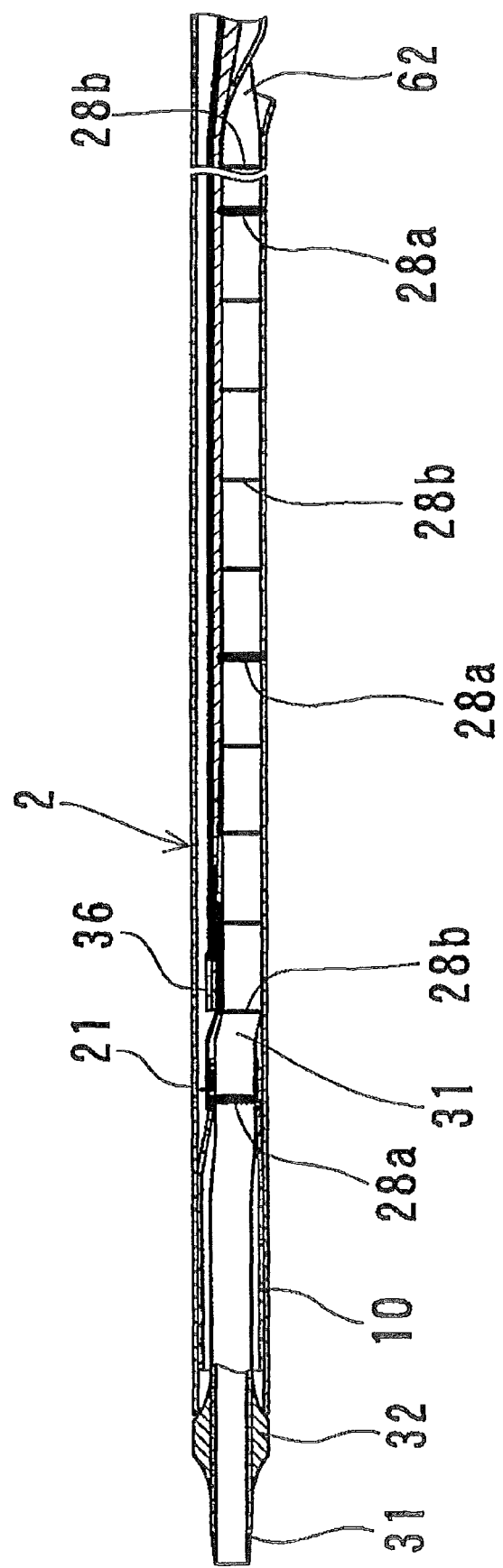
FIG. 7 is an explanatory illustration of the inner tube of the delivery system shown in FIG. 1.
Figure 8:
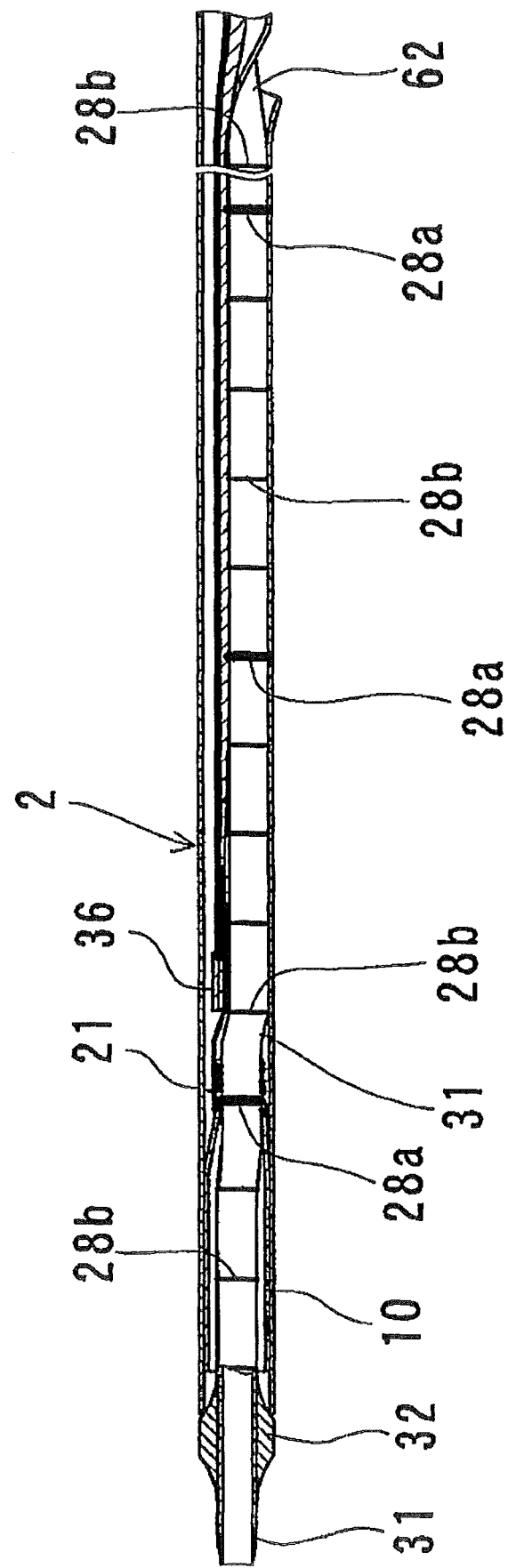
FIG. 8 is an explanatory illustration of the inner tube of a stent delivery system according to another embodiment disclosed here.

Specifically, as shown in FIGS. 1, 4 and 7, the distal-side tube 31 of the inner tube 3 has the radiopaque indication region which extends proximally over a distance of at least 5 mm from the proximal end of the stent 10 (specifically, a position coinciding with the proximal end of the stent or a position adjacent to the proximal end of the stent). The distance over which the terminal point of the radiopaque indication region is proximally spaced from the proximal end of the stent 10 is preferably at least 8 mm, more preferably in excess of 10 mm. In this embodiment, the radiopaque indication region has its starting point at the proximal end of the stent 10 as above-mentioned.

The radiopaque indication region is provided with the distance indicating function. Specifically, the plurality of radiopaque markers 28a, 28b arranged so as to be mutually spaced at a predetermined interval are provided in the radiopaque indication region. This makes it possible for the distance from the proximal end of the stent 10 to be checked under radiography. In addition, in the delivery system according to this embodiment, the plurality of radiopaque markers 28a, 28b are scale-like or scale-forming radiopaque markers provided at equal intervals. Therefore, by checking the number of the radiopaque markers, it is possible to check the distance from the proximal end of the stent 10 mentioned above. The interval (distance) between immediately adjacent ones of the radiopaque markers 28a, 28b is preferably about 0.5 to 1.5 mm, more preferably 1.0 mm. Further, the radiopaque markers 28a, 28b preferably include a plurality of main scales 28a and a plurality of auxiliary scales 28b, with the auxiliary scales 28b located between the main scales 28a and lower in radiopacity than the main scales 28a. This facilitates counting of the markers and, hence, grasping of the distance. As illustrated, the main scales 28a can also be configured to be visually distinguishable and visually different from the auxiliary scales 28b. The interval or distance between the adjacent main scales 28a is preferably 2 to 5 mm, and the number of auxiliary scales 28b positioned between the adjacent main scales 28a is preferably in the range of 1 to 4. In this embodiment, the auxiliary scales 28b are smaller in width (line width) than the main scales 28a, and are lower in radiopacity than the main scales 28a. The auxiliary scales may be formed from a material lower in radiopacity than the material forming the main scales so as to be lower in radiopacity than the main scales. In this case, both the scales may possess the same line width.

In addition, the starting point of the radiopaque indication region is not limited to the position corresponding to the proximal end of the stent 10 mentioned above. For instance, as illustrated by the stent delivery system shown in FIG. 8, the starting point of the radiopaque indication region may be located at a position corresponding to the distal end of the stent 10 (specifically, a position coinciding with the distal end of the stent or a position adjacent to the distal end of the stent). The radiopaque indication region can also be configured and positioned so that the starting point of the radiopaque indication region corresponds to a middle portion of the stent 10.

In the delivery system 1 in this embodiment, the inner tube 3 (specifically, the distal-side tube 31) has the proximal opening 62 communicating with the guide wire lumen on the proximal side relative to the stent accommodating portion of the stent accommodating tube 2, and the radiopaque indication region preferably extends to the vicinity of the proximal opening 62. In the delivery system according to the embodiment shown in FIGS. 7 and 8, the radiopaque marker on the most proximal side is located in the vicinity of the proximal opening 62 of the distal-side tube 31.

The radiopaque markers 28a, 28b may be any markers that can offer good radiopacity. Particularly, the radiopaque markers 28a, 28b are preferably formed from a radiopaque metal (e.g., gold, platinum, tungsten or their alloys, or silver-palladium alloy or the like). Preferably, a ring-shaped member formed from such a metal is fixed on the inner tube 3 (specifically, the distal-side tube 31) by caulking, winding or the like. In addition, the radiopaque markers 28a, 28b can be formed from a material which is the same as or compatible with the material forming the distal-side tube 31, or from a material which is obtained by adding a radiopaque substance to a material capable of forming a coating film on the distal-side tube 31 (e.g., a film-forming silicone compound, a film-forming urethane compound). Examples of the radiopaque substance include radiopaque materials such as barium sulfate, bismuth oxide, and powders of the above-mentioned radiopaque metals.

In addition, as shown in FIGS. 5 and 6, the distal-side tube 31 preferably has a reinforcement layer 31a provided at least at a portion constituting the radiopaque indication region. In this embodiment, the reinforcement layer 31a is provided over the whole part of the distal-side tube 31. A structure may be adopted in which the reinforcement layer 31a is not provided on a most distal portion of the distal-side tube 31. With the reinforcement layer provided at the portion constituting the radiopaque indication region, the tube constituting this portion is restrained from compressive deformation, kinking or meandering, so that accurate grasping or determination of distance can be realized.

The reinforcement layer 31a is preferably a network-formed reinforcement layer. The network-formed reinforcement layer is preferably formed of braid wire. An example is a wire braid, which can be formed of metallic wire of stainless steel, an elastic metal, a superelastic metal, a shape memory alloy or the like having a diameter of 0.01 to 0.2 mm, preferably 0.03 to 1.0 mm. Alternatively, the network-formed reinforcement layer may be formed of synthetic fiber such as polyamide fiber, polyester fiber, polypropylene fiber, etc.

The shaft body 33 includes a distal portion fixed to a proximal portion of the distal-side tube 31, a body portion extending proximally from the distal portion over a predetermined length, and a proximal portion extending proximally from the body portion and protruding proximally from the shaft hub 30. In this embodiment, the shaft body 33 is configured such that a distal portion corresponding to a portion fixed to the distal-side tube 31 is a relatively smaller diameter portion, and the body portion and the proximal portion are relatively larger diameter portions having a greater outside diameter than the smaller diameter distal portion. In this embodiment, the distal portion of the shaft body 33 is fixed to a side surface of the distal-side tube 31 by a heat-shrinking tube 63 as generally shown in FIG. 6.

The length of the shaft part 3 is preferably about 400 to 2500 mm, more preferably 400 to 2200 mm. The outside diameter of the body portion of the shaft body 33 is preferably about 1.0 to 2.5 mm, more preferably 1.0 to 2.0 mm. The length of the distal-side tube 31 is preferably about 10 to 400 mm, more preferably 50 to 350 mm. The outside diameter of the distal-side tube 31 is preferably about 0.2 to 2.0 mm. The inside diameter of the lumen 61 is preferably 0.2 to 2.0 mm, more preferably 0.3 to 1.0 mm.

The shaft body 33 may be either solid or tubular. In addition, the shaft body 33 may be a coil shaft. The material forming the shaft part 3 is preferably a material which is hard and, at the same time, has a certain degree of flexibility. Preferable examples of such a material include metallic wire or metallic pipe of stainless steel, superelastic metal or the like, and solid material or tubular material of polyethylene, polypropylene, nylon, polyethylene terephthalate, fluoropolymer such as ETFE, etc., PEEK (polyether-ether ketone), polyimide or the like. The outer surface of the shaft part 3 may be coated with a material which has biocompatibility, particularly anti-thrombic property. Preferable examples of the anti-thrombic material include polyhydroxyethyl methacrylate, hydroxyethyl methacrylate-styrene copolymer (e.g., HEMA-St-HEMA block copolymer), etc.

Further, the outer surface of that portion of the shaft part 3 which may possibly protrude from the sheath 2 preferably has lubricity. For realizing this, a hydrophilic polymer such as poly(2-hydroxyethyl methacrylate), polyhydroxyethyl acrylate, hydroxypropyl cellulose, methyl vinyl ether-maleic anhydride copolymer, polyethylene glycol, polyacrylamide, polyvinyl pyrrolidone, etc. may be applied or fixed to the outer surface of the shaft part 3. Besides, the hydrophilic polymer may be applied or fixed to the whole outer surface of the shaft part 3. Furthermore, the hydrophilic polymer may also be applied or fixed to the inner surface of the shaft part 3, for enhancing the slidability between the inner surface and a guide wire.

The shaft body 33 penetrates the sheath 2, and protrudes proximally from the proximal end opening of the sheath 2. The shaft hub 30 is secured to the proximal end of the shaft body 33 as shown in FIGS. 1-3 and 10. In this embodiment, a fixed ring (first fixed ring) 66 is fixed to the shaft body 33, as shown in FIG. 9. In addition, a proximal tube 34 is fixed to the shaft hub 30 and extends in the distal direction relative to the shaft hub 30. A distal portion of the proximal tube 34 is fixed to the fixed ring 66. An elastic ring 69 is fixed to the proximal end of the proximal tube 34 at a position inside the shaft hub 30. Further, in this embodiment, another fixed ring (second fixed ring) 68 is provided at a position spaced a predetermined distance in the distal direction from the fixed ring 66. An intermediate tube 67 is disposed between the one fixed ring 66 and the other fixed ring 68. The intermediate tube 67 is fixed to neither the shaft body 33 nor the sheath tube 21, and is capable of abutting against the one fixed ring 66 and the other fixed ring 68. The intermediate tube 67 helps enhance slidability of the sheath. The intermediate tube 67 preferably has a low-friction outer surface. The intermediate tube 67 is preferably formed from, for example, polyethylene, polypropylene, nylon, polyethylene terephthalate, a fluoro-polymer such as PTFE, ETFE, etc.

Figure 11:
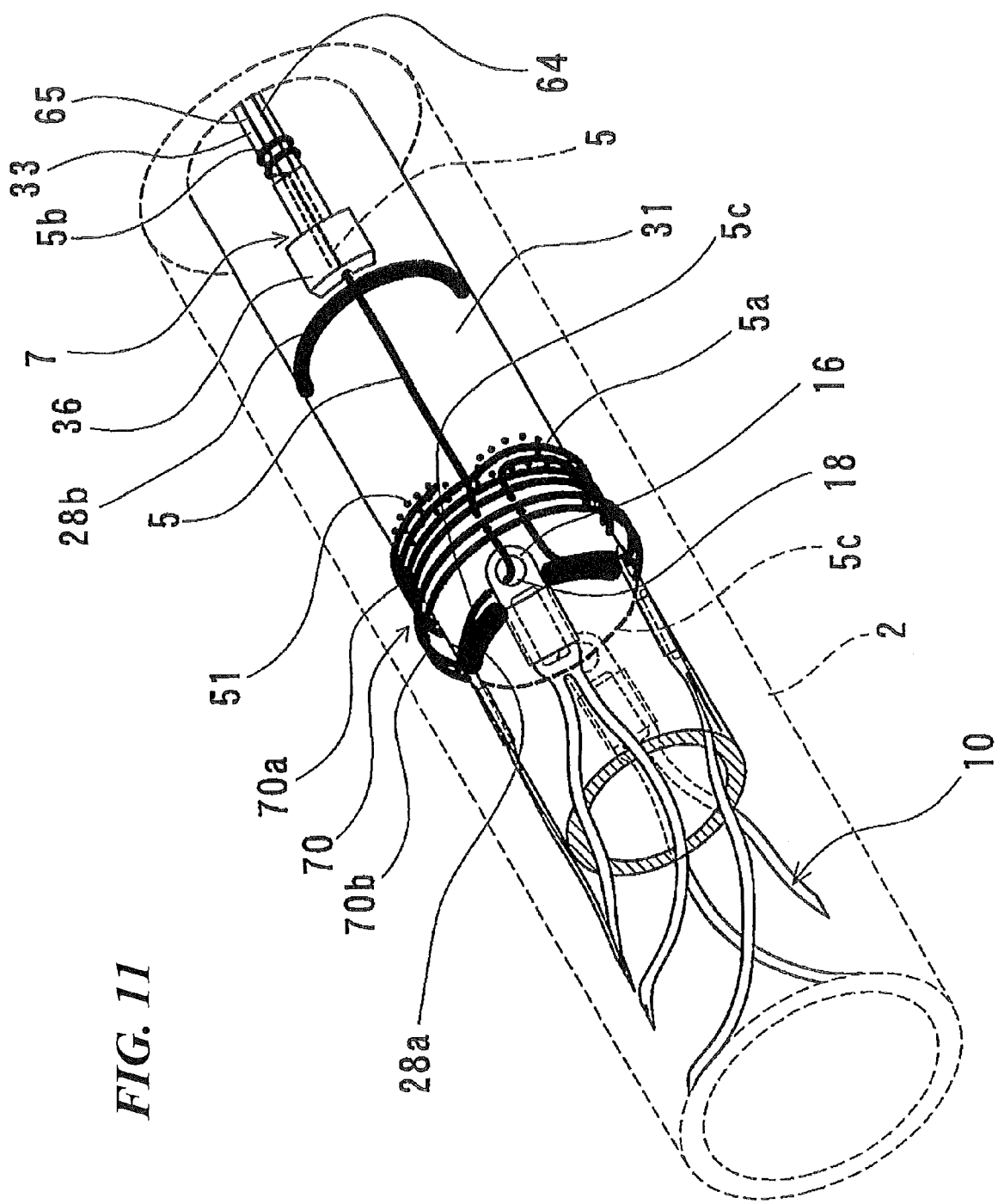
FIG. 11 is a perspective view illustrating the proximal end of a stent of the delivery system shown in FIG. 1.
Figure 16:
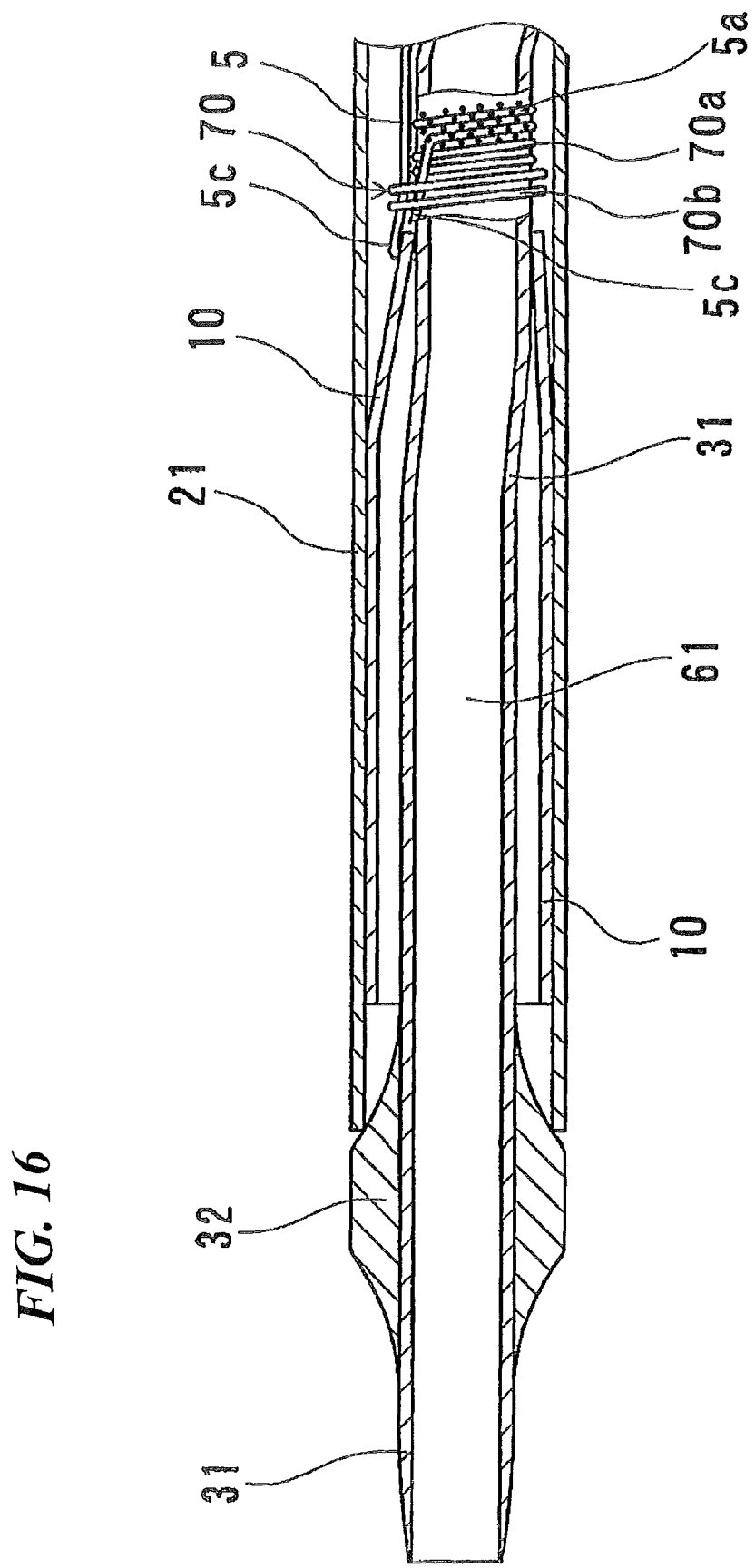
FIG. 16 is an enlarged longitudinal cross-sectional view of the distal portion of a stent delivery system according to a further embodiment.

Furthermore, as shown in FIGS. 5 and 11, at a distal portion of the shaft part 3 (specifically, at a proximal portion of the distal-side tube 31, in other words in the vicinity of the proximal end of the stent disposing part), a proximal-side stopper 70 is provided for restricting the movement of the stent 10 in the proximal direction. In this embodiment, the proximal-side stopper 70 is a spring-formed stopper wound around the shaft part 3. As shown in FIGS. 5 and 11, the proximal-side stopper 70 has a proximal-side coil part 70a wound around the distal-side tube 31, and a distal-side coil part 70b which extends in the distal direction from the proximal-side coil part 70a and has a partial non-contact portion not in contact with the distal-side tube 31. The distal-side coil part 70b in this embodiment is eccentrically fixed to the distal-side tube 31, and has a portion in contact with the distal-side tube 31 and a portion spaced from the distal-side tube 31. The stent proximal end fixing linear member 5 penetrates the non-contact portion that is not in contact with the distal-side tube 31. In addition, the linear member 5 extending toward the stent 10 from the one end portion 5a of the linear member 5 may be fixed to the distal-side coil part 70b. The fixation of the linear member 5 to the distal-side coil part 70b is preferably achieved by gripping (clamping) between coils. The distal-coil part 70b acts as a stopper for the stent 10. Further, the distal-side coil part 70b may be one that is wholly spaced from the distal-side tube 31, as in an embodiment shown in FIG. 16.

The distal-side coil part 70b is spring-shaped, and can be locked to a proximal end of the stent 10 without damaging the latter. In addition, the stopper 70 may be formed of a radiopaque material. This helps ensure that the position in the vicinity of the proximal end of the stent 10 can be determined under radiography, thereby providing easier use.

The radiopaque material is preferably, for example, gold, platinum, platinum-iridium alloy, silver, stainless steel, one of their alloys, or the like. The stopper 70 can be fabricated by forming a radiopaque material into wire, and winding the wire around the outer surface of the distal-side tube 31.

Furthermore, as shown in FIGS. 4-6 and 11, the shaft part 3 includes the heat-rupturing stent proximal end fixing linear member 5 which has its one end portion 5a and its other end portion 5b fixed to the shaft 3 and has its intermediate portion 5c moored or fixed to a proximal end of the stent 10, and the heat-rupturing part 7 for rupturing the stent proximal end fixing linear member 5 and thereby releasing the mooring, fixation or securement of the stent 10.

Particularly, in this embodiment, as shown in FIG. 11, the stent 10 has a plurality of small holes 18 through which pass the stent proximal end fixing linear member 5. In this illustrated embodiment, these small holes 18 are positioned in a connection part 16 on the proximal end of the stent. The intermediate portion 5c of the stent proximal end fixing linear member 5 passes sequentially through the plurality of holes 18 in the stent 10, and, as a whole, passes through the plurality of holes 18 in an annular fashion. Therefore, the stent 10 is moored (fixed) to the shaft part 3 by the stent proximal end fixing linear member 5 so that the stent 10 is not disconnected from the shaft part 3 unless the stent proximal end fixing linear member 5 is ruptured (cut).

In this embodiment, the one end portion 5a of the stent proximal end fixing linear member 5 is wound around the outer surface of the distal-side tube 31 and is fixed to the outer surface of the distal-side tube 31 by an adhesive 51, in the vicinity of and slightly on the proximal side of the stopper 70. In addition, the other end portion 5b of the stent proximal end fixing linear member 5 is wound around and fixed to the outer surface of the shaft body 33.

The one end portion 5a and the other end portion 5b of the stent proximal end fixing linear member 5 are not limited to portions wound around and fixed to the outer surfaces of the distal-side tube 31 and the shaft body 33, respectively. The one end portion 5a and the other end portion 5b of the stent proximal end fixing linear member 5 may be fixed respectively to the outer surfaces of the distal-side tube 31 and the shaft body 33 by, for example, caulking rings. Furthermore, in this embodiment, the stent proximal end fixing linear member 5 extends in the direction of the stent 10 while passing through a gap in the coil constituting the spring-formed stopper 70 from the one end portion 5a and the other end portion 5b which are fixed to the shaft part 3. Specifically, both that portion of the stent proximal end fixing linear member 5 which extends from the one end portion 5a and that portion of the stent proximal end fixing linear member 5 which extends from the other end portion 5b extend while passing over the proximal-side coil part 70a of the stopper 70 and penetrating the distal-side coil part 70b. With the stopper 70 formed in this manner, the stopper functions as a stopper for the stent proximal end portion, and by penetrating the stent fixing linear member 5, relatively reliable fixation of the stent 10 by the wire 5 is realized, and the wire 5 can be inhibited or prevented from becoming entangled around the stent 10 at the time of being released from the stent 10 so that the releasing can be securely performed.

The heat-rupturing stent proximal end fixing linear member 5 is preferably a fiber made of a thermoplastic resin. The thermoplastic resin is preferably a synthetic resin such as polyethylene, polypropylene, nylon, polyethylene terephthalate, etc., among which particularly preferred are those which have a low melting point. In addition, the heat-rupturing stent proximal end fixing linear member 5 may have a structure in which only its portion near the portion to be heat ruptured is formed of the low-melting-point resin. Also, the heat-rupturing stent proximal end fixing linear member 5 may be composed of a single thermoplastic resin fiber or composed of a plurality of thermoplastic resin fibers bundled or twisted together.

The shaft part 3 has the heat-rupturing part 7 for rupturing the stent proximal end fixing linear member 5 and thereby releasing the mooring of the stent 10. In this embodiment, the heat-rupturing part 7 is composed of a rupture heat generating part 36, electric cables 64, 65 having distal ends connected to the heat generating part 36 and extending in the proximal portion of the shaft body 33, and a connection part 35 for connection with a power supply. The connection part 35 is connected to the electric cables 64, 65 and is formed at a proximal portion of the shaft body 33.

In this embodiment, the rupture heat generating part 36 of the heat-rupturing part 7 is fixed to the distal end of the shaft body 33, and the electric cables 64, 65 extend to a proximal portion of the shaft body 33 in the state of being fixed to the outer surface of the shaft body 33.

Figure 10:
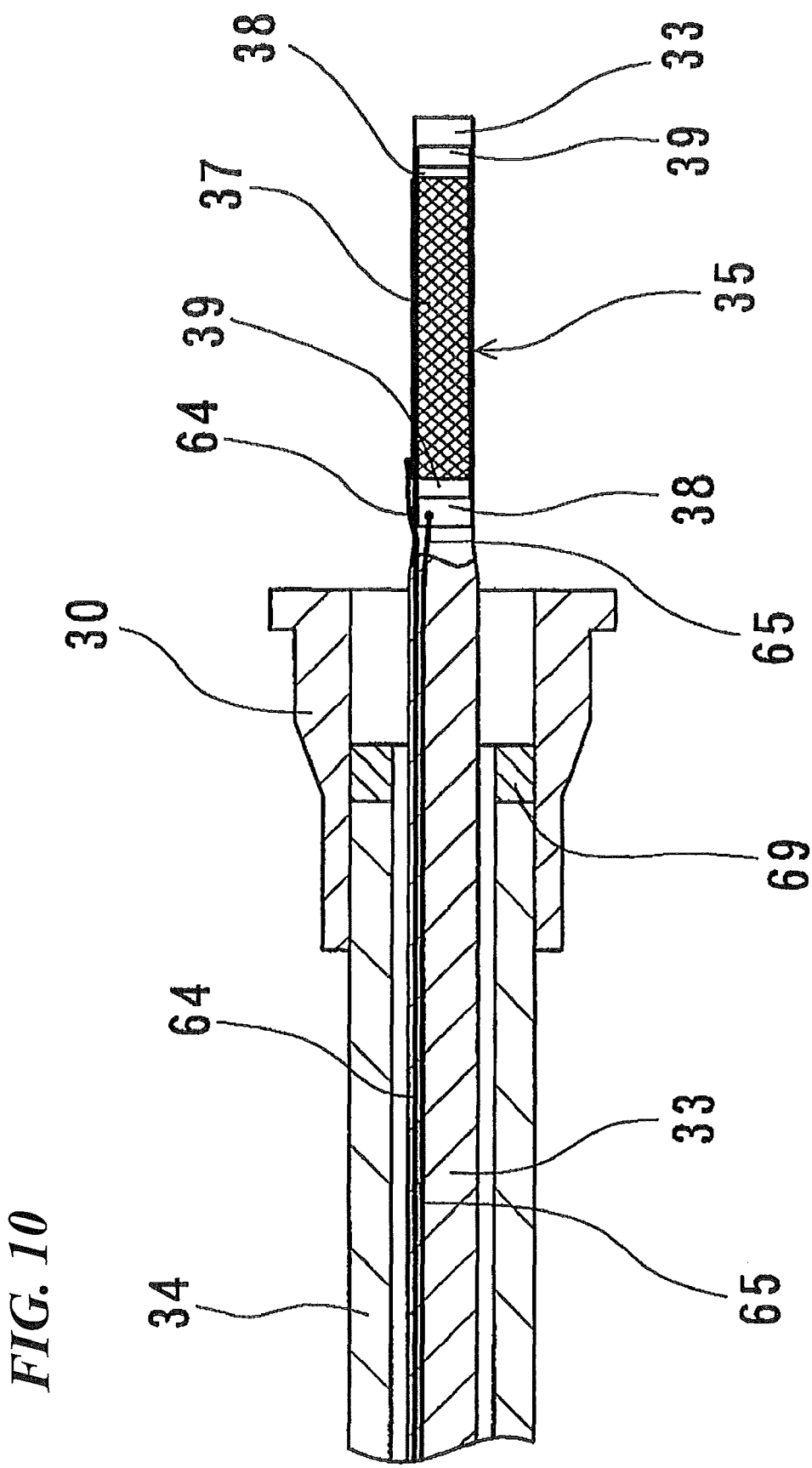
FIG. 10 is an enlarged longitudinal cross-sectional view of the proximal portion of a shaft part of the delivery system shown in FIG. 1.

As shown in FIG. 10, the connection part 35 for connection with the power supply (not shown) is formed at a proximal portion of the shaft body 33. The connection part 35 is formed on the outer surface of a proximal portion of the shaft body 33, and includes a first electrode part 37 electrically connected to the cable 64, and a second electrode 38 connected to the cable 65. In this embodiment, an insulation part 39 provides insulation between the first electrode 37 and the second electrode 38. A portion of the heat-rupturing stent proximal end fixing linear member 5, in this embodiment that portion which is deviated from the other end portion 5b toward the intermediate portion by a predetermined length, is enveloped by the rupture heat generating part 36. Under electric power supplied to the first electrode part 37 and the second electrode 38 of the connection part 35, the rupture heat generating part 36 generates heat, to melt and rupture the heat-rupturing stent proximal end fixing linear member 5 at that portion.

The stent 10 used here is a so-called self-expandable stent which, when left indwelling in vivo, can automatically expand outwardly to restore its pre-compression shape. Further, the stent 10 has a distal end directed toward the distal side of the sheath 2 and a proximal end directed toward the proximal side of the sheath 2, but does not substantially have a free bent portion projecting toward the proximal side, except for the proximal end. By moving the sheath 2, after the distal end of the stent 10 is exposed from the sheath 2, the exposed distal end can again be accommodated into the sheath 2.

Figure 12:
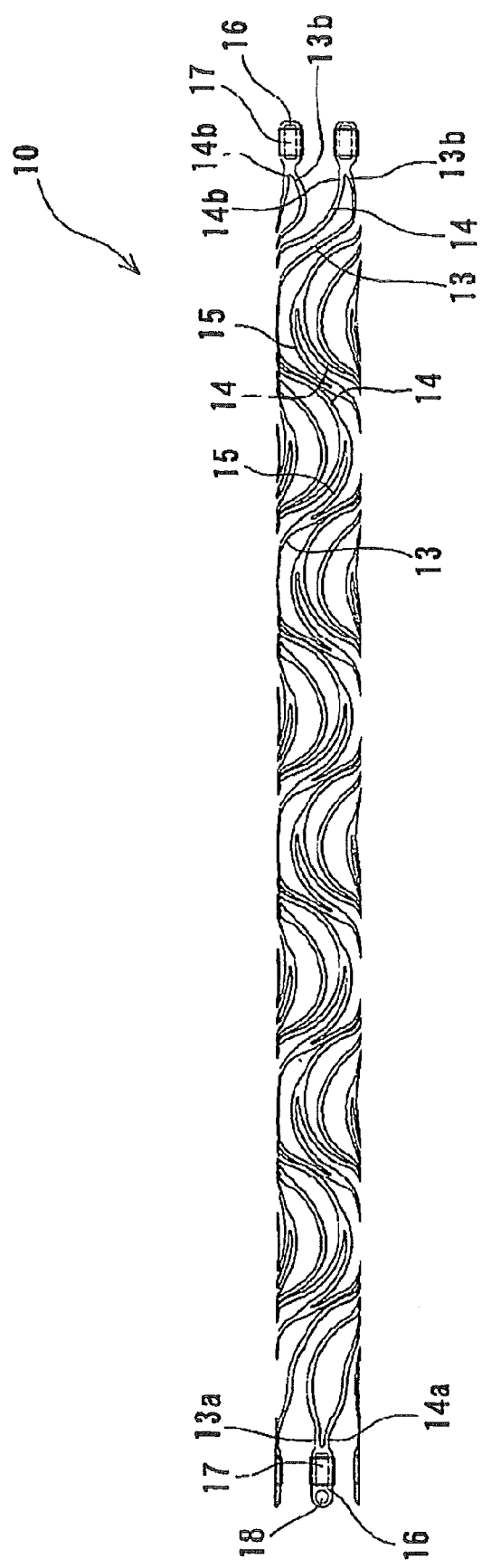
FIG. 12 is a side view of an example of a stent used in the delivery system according to an embodiment disclosed here.
Figure 13:
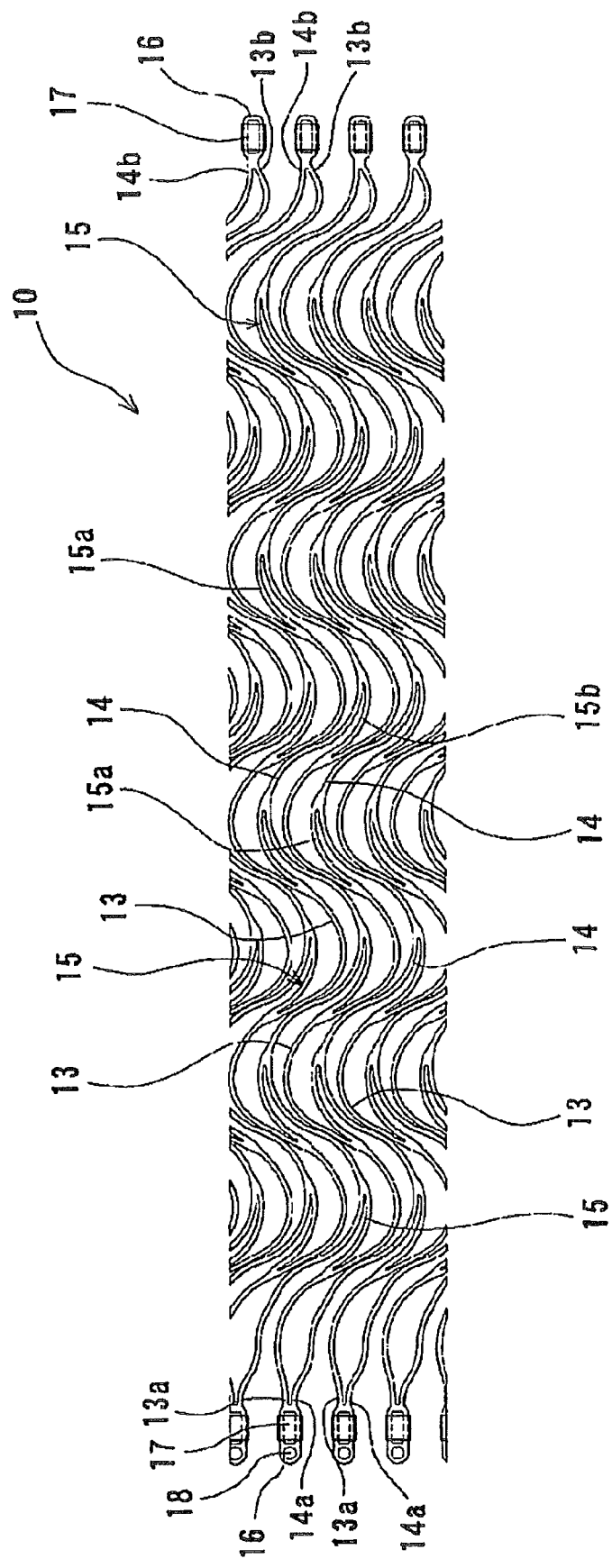
FIG. 13 is a developmental view of the stent shown in FIG. 12 illustrating the stent cut along its length and flattened out.

The stent 10 may be one as shown in FIGS. 12 and 13. FIG. 12 is a front view of an example of a stent used in the delivery system according to an embodiment disclosed here and FIG. 13 is a development view of the stent shown in FIG. 12 illustrating the configuration of the stent when cut along its longitudinal extent and then flattened.

The stent 10 includes wavy struts 13 and 14 extending in the axial direction from one end side (proximal end) to the other end side (distal end) of the stent 10, with plural wavy struts arrayed along the circumferential direction, and one or a plurality of connecting struts 15 interconnecting the adjacent wavy struts 13, 14 and extending in the axial direction over a predetermined length. Further, end portions of the wavy struts 13, 14 are coupled to end portions of adjacent wavy struts.

Particularly, the stent 10 shown in FIGS. 12 and 13 is composed of the first wavy struts 13 extending in the axial direction from one end side to the other end side of the stent 10 and arrayed in plural manner along the circumferential direction, the second wavy struts 14 each located between the first wavy struts 13, extending in the axial direction from one end side to the other end side of the stent 10 and arrayed in plural manner in the circumferential direction, and one or a plurality of connecting struts 15 each interconnecting the first wavy strut 13 and the second wavy strut 14 adjacent to each other and extending over a predetermined length in the axial direction. The vertices of the second wavy struts 14 are deviated by a predetermined distance in the axial direction of the stent 10 from those vertices of the first wavy struts 13 which are circumferentially adjacent and curved in the same direction. In addition, end portions 13a, 13b of the first wavy struts 13 are coupled respectively to those end portions 14a, 14b of the second wavy struts 14 which are adjacent thereto.

The stent 10 in this embodiment is a so-called self-expandable stent which is formed in a substantially hollow cylindrical shape, is compressed toward its center axis when inserted in vivo, and restores its pre-compression shape through expanding outwards when left indwelling in vivo.

The first wavy struts 13 extend in the axial direction substantially in parallel to the center axis of the stent 10. The first wavy struts 13 are arrayed in plurality along the circumferential direction of the stent 10. The number of the first wavy struts 13 is preferably at least three, more preferably in the range of about 3 to 8. Further, the plurality of the first wavy struts 13 are preferably arranged so that they are at substantially equal angles to the center axis of the stent 10.

The second wavy struts 14 also extend in the axial direction substantially in parallel to the center axis of the stent 10. The second wavy struts 14 are arrayed in plurality along the circumferential direction of the stent 10, and each of the second wavy struts 14 is arranged between the first wavy struts 13. The number of the second wavy struts 14 is preferably at least three, more preferably in the range of about 3 to 8. Further, the plurality of the second wavy struts 14 are preferably arranged so that they are at substantially equal angles to the center axis of the stent 10. Besides, the number of the second wavy struts 14 is equal to the number of the first wavy struts 13.

In addition, the stent 10 has one or a plurality of connecting struts 15 which interconnect the first wavy struts 13 and the second wavy struts 14 adjacent to each other and extend over a predetermined length in the axial direction. Particularly, in the stent 10 in this embodiment, the connecting strut 15 has its one end in the vicinity of an inflection point of the wavy strut on one side, has its other end in a region in the vicinity of or slightly beyond a vertex of the adjacent wavy strut on the other side, extends in the axial direction, and is curved in the same direction as the vertex of the wavy strut on the other side. Specifically, as shown in FIG. 13, the connecting struts 15 are composed of first curved connecting struts 15a which have vertexes directed to one side in the circumferential direction of the stent 10, and second curved connecting struts 15b which have vertexes directed to the other side in the circumferential direction of the stent 10. In addition, the connecting strut 15 is curved in an arcuate shape, and has a radius substantially equal to that of the arcuate shape of a curved portion of the first wavy strut 13 or the second wavy strut 14 which is adjacent thereto. The stent 10 in this embodiment has a coupling part 16 by which a one-side end portion and an other-side end portion of the first wavy strut is coupled to either one of end portions of the second wavy strut adjacent thereto.

Specifically, a one-end-side end portion 13a of the first wavy strut 13 of the stent 10 is coupled by the coupling part 16 to a one-side end portion 14a of the second wavy strut 14 on one side adjacent to the first wavy strut 13 (more specifically, the second wavy strut 14 adjacent to, and located on the other side in the circumferential direction of, the first wavy strut 13). An other-end-side end portion 13b of the first wavy strut 13 is coupled by the coupling part 16 to an end portion 14b of the second wavy strut 14 on one side adjacent to the first wavy strut 13 (more specifically, the second wavy strut 14 adjacent to, and located on one side in the circumferential direction of, the first wavy strut 13). In short, the coupling part 16 on one end side and the coupling part 16 on the other end side differ (shifted by one at a time) in the combination of the first wavy strut 13 and the second wavy strut 14 coupled to each other.

Figure 14:
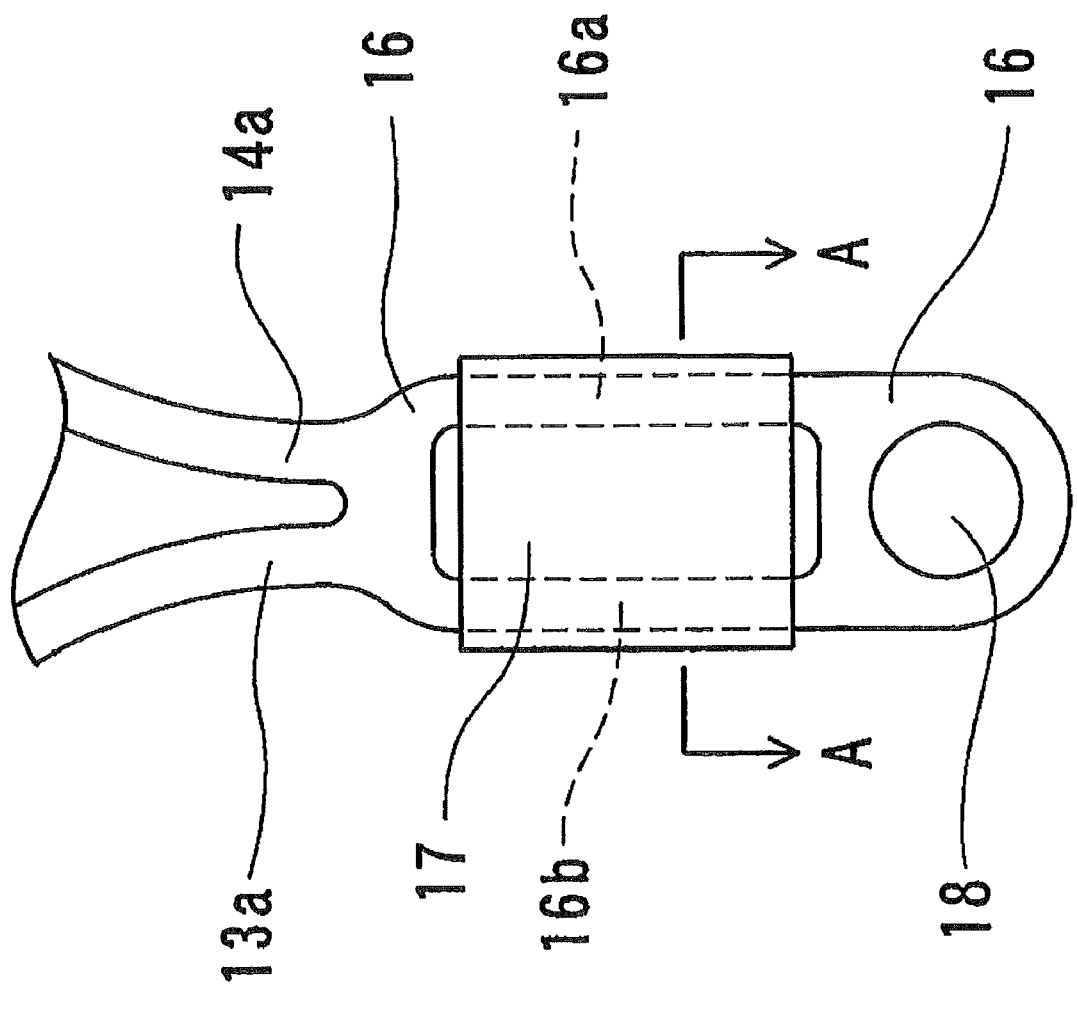
FIG. 14 is an enlarged view of the proximal end of the stent shown in FIG. 12 in the region of the holes.
Figure 15:
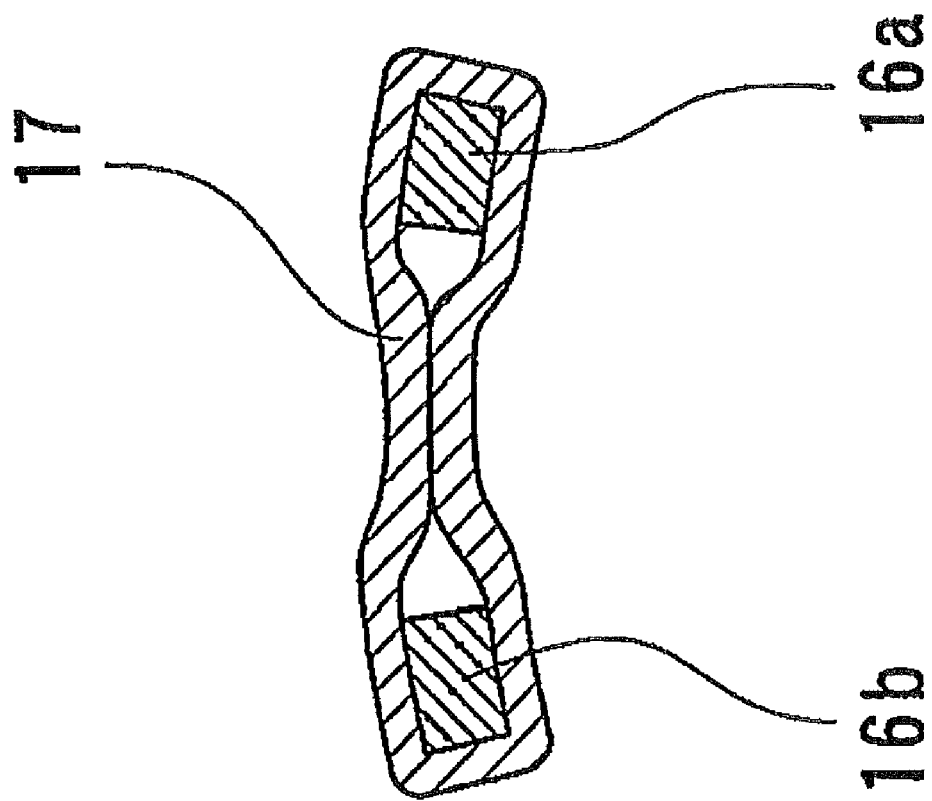
FIG. 15 is an enlarged cross-sectional view taken along the section line XV-XV in FIG. 14.

As shown in FIGS. 12-14, a radiopaque marker 17 is attached to the coupling part 16. In this embodiment, as shown in FIG. 14, the coupling part 16 has two frame portions 16a, 16b mutually spaced by a predetermined distance in the direction of the end portion and extending parallel to each other, and the radiopaque marker 17 envelopes the two frame portions 16a, 16b substantially wholly or partly. The radiopaque marker 17 possesses a thin rectangular parallelepiped shape, accommodates the two frame portions 16a, 16b therein, and has its central portion depressed, whereby the radiopaque marker 17 is fixed to the two frame portions 16a, 16b. As the material for forming the radiopaque marker 17, there can be suitably used one (element) or at least two (alloy) selected from the group consisting of iridium, platinum, gold, rhenium, tungsten, palladium, rhodium, tantalum, silver, ruthenium, and hafnium.

Furthermore, in the stent 10, each coupling part 16 on the end side constituting a proximal end is provided with the small hole 18 permitting the stent proximal end fixing linear member 5 to pass therethrough. The small hole 18 is directed to the central axis of the stent 10. The small hole 18 preferably has a low-friction inner surface or an easily releasable form for enhancing the release (disconnection) property for the stent proximal end fixing linear member 5. The low-friction inner surface can be formed by making the inner surface smooth or by coating the inner surface with a low-friction material.

Figure 17:
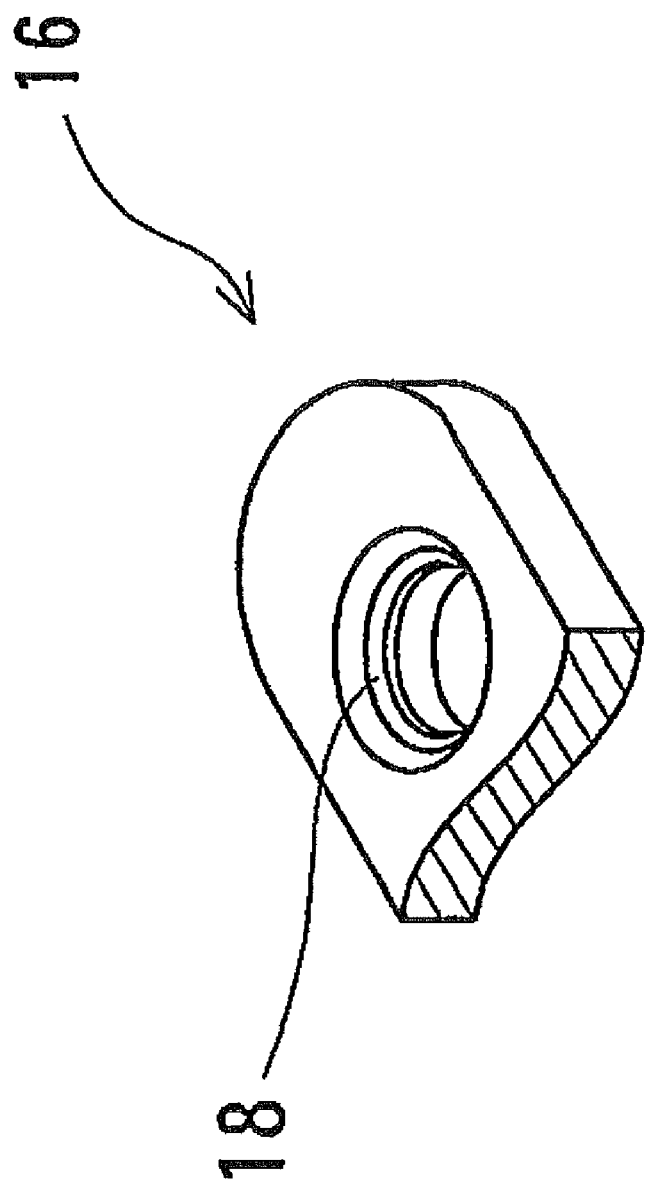
FIG. 17 is an enlarged perspective view of the proximal end of the stent, in the vicinity of the holes, used in the delivery system according to the embodiment disclosed here.

As the easily releasable form of the small hole 18, the one shown in FIG. 17 may be considered. In the small hole 18 formed in the coupling part 16 shown in FIG. 17, an aperture edge of the small hole 18 is chamfered or tapered to be enlarged in diameter. The aperture edges of the small hole 18 which are located respectively on both the outer surface side and the inner surface side of the stent 10 may be chamfered or tapered to be enlarged in diameter. This structure of the small hole 18 facilitates passage of the stent proximal end fixing linear member 5 and release of the stent proximal end fixing linear member 5.

As the material constituting the stent 10, a superelastic metal is used preferably. As the superelastic metal, a superelastic alloy is preferably used. The superelastic alloy here means an alloy which is referred to as a shape memory alloy and which exhibits superelasticity at least at a living body temperature (around 37° C.). Particularly preferable examples include superelastic metallic alloys such as Ti—Ni alloys containing 49 to 52 wt % of Ni, Cu—Zn alloys containing 38.5 to 41.5 wt % of Zn, Cu—Zn—X alloys (X=Be, Si, Sn, Al, or Ga) containing 1 to 10 wt % of X, and Ni—Al alloys containing 36 to 38 wt % of Al. Among these materials, Ti—Ni alloys are especially preferable. Mechanical properties of the material for the stent 10 can be changed, as required, by using as the material a Ti—Ni—X alloy (X=Co, Fe, Mn, Cr, V, Al, Nb, W, or B) obtained by replacing part of a Ti—Ni alloy with 0.01 to 10.0% of X, or by using as the material a Ti—Ni—X alloy (X=Cu, Pb, or Zr) obtained by replacing part of a Ti—Ni alloy with 0.01 to 30.0% of X, or by selecting the cold working ratio or/and final heat treatment conditions. While using the Ti—Ni—X alloy, mechanical properties can be changed as required by selecting the cold working ratio and/or final treatment conditions. The superelastic alloy to be used here has a buckling strength (yield stress when loaded) of 5 to 200 kg/mm$^2$ (22° C.), preferably 8 to 150 kg/mm$^2$, and a restoring stress (yield stress when unloaded) of 3 to 180 kg/mm$^2$ (22° C.), preferably 5 to 130 kg/mm$^2$. Superelasticity here means that even when the material is deformed (bent, stretched, or compressed) into a region where ordinary metals are plastically deformed, at a use temperature, the deformed material will, after release of the deformation, substantially restore its pre-deformation shape without the need for heating.

The diameter of the stent when compressed is preferably about 0.5 to 1.8 mm, more preferably 0.6 to 1.4 mm. The length of the stent when not compressed is preferably about 5 to 200 mm, more preferably 8.0 to 100.0 mm. The diameter of the stent when not compressed is preferably about 1.5 to 6.0 mm, more preferably 2.0 to 5.0 mm. Further, the material thickness of the stent is preferably about 0.05 to 0.15 mm, more preferably 0.05 to 0.40 mm. The width of the wavy struts is preferably 0.01 to 1.00 mm, more preferably 0.05 to 0.2 mm. The surfaces of the wavy struts are preferably processed to be smooth, more preferably smoothened by electropolishing. In addition, the strength of the stent in the radial direction is preferably 0.1 to 30.0 N/cm, more preferably 0.5 to 5.0 N/cm.

Figure 19:
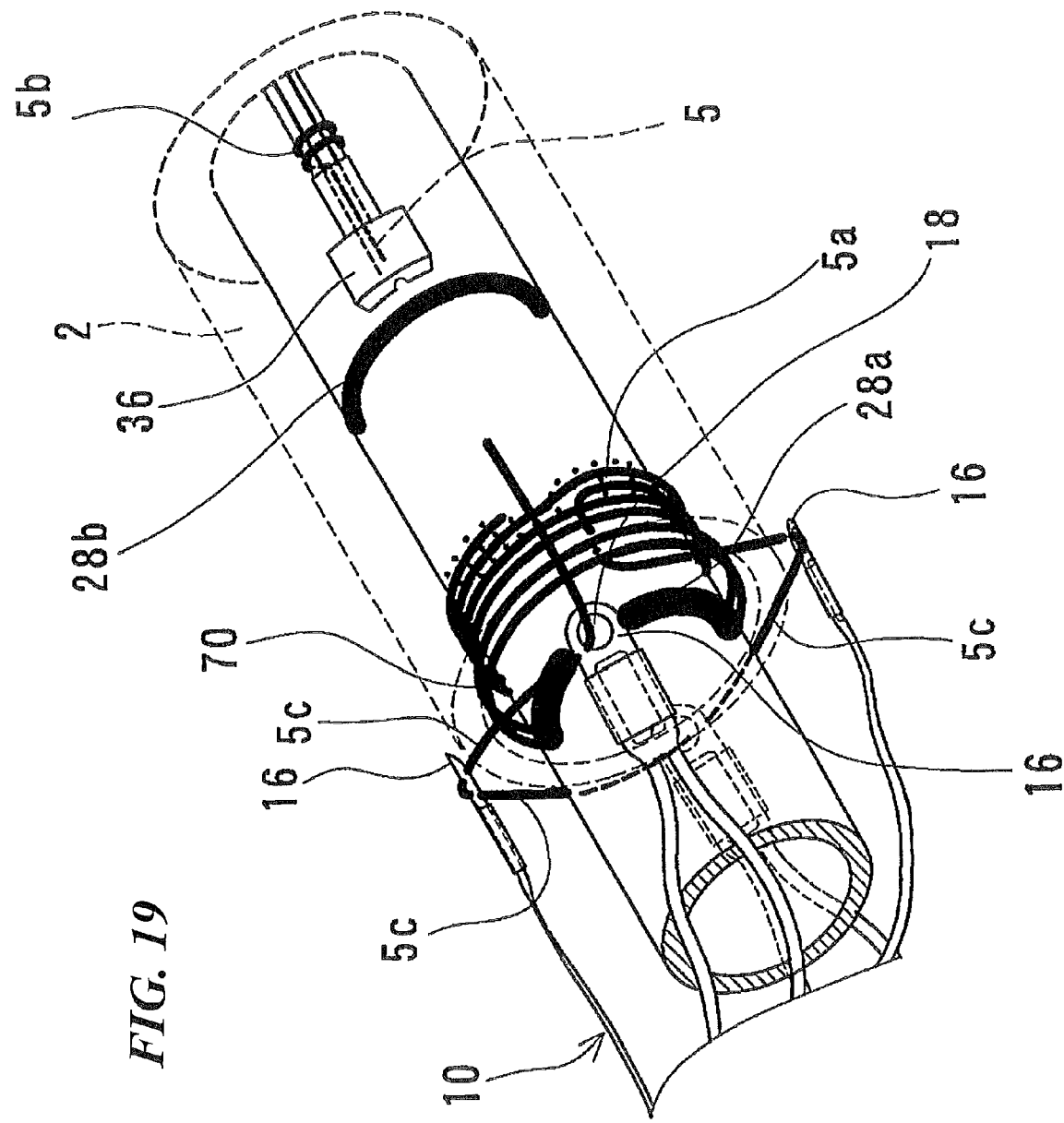
Figure 20:
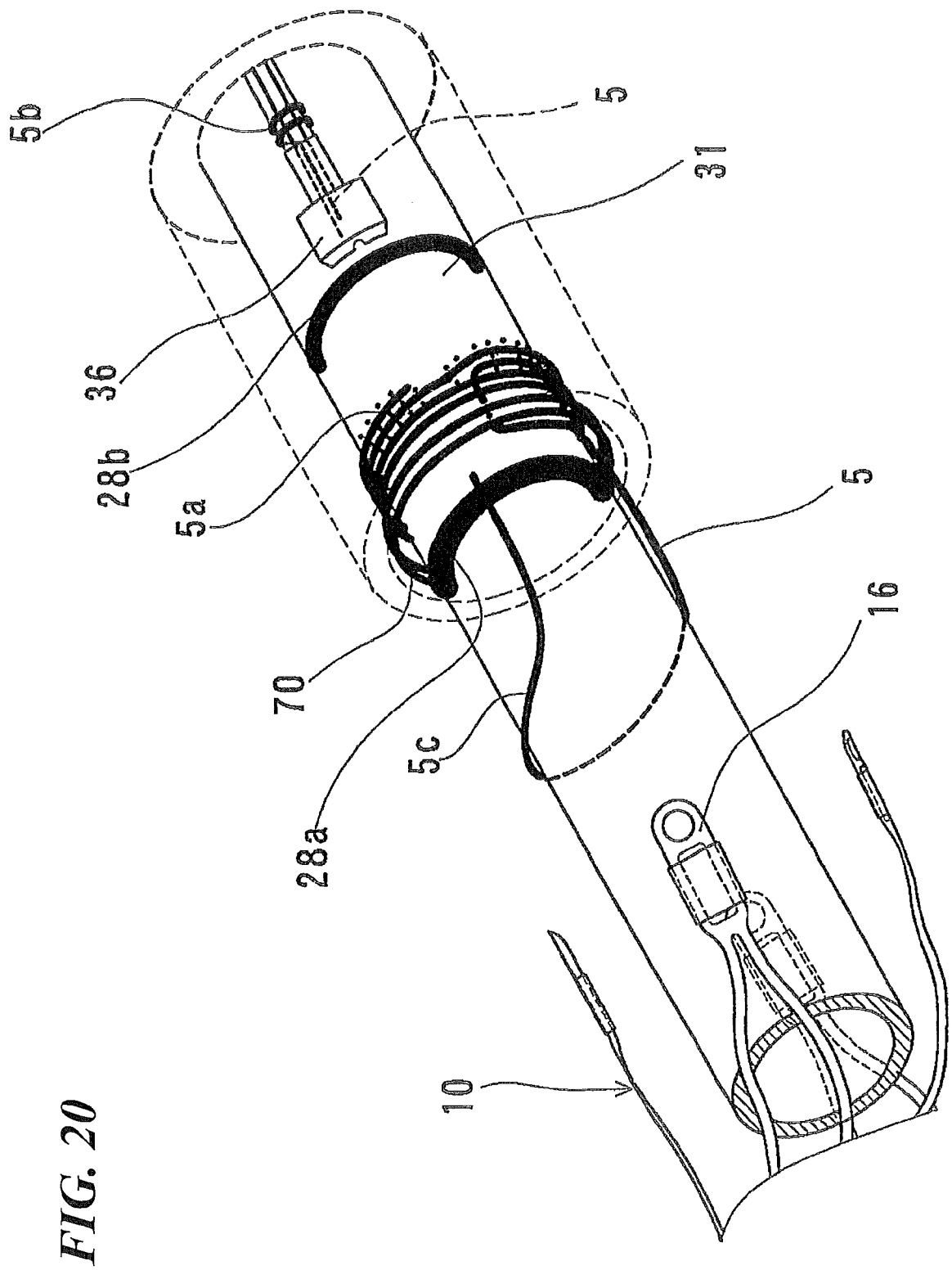
Figure 21:
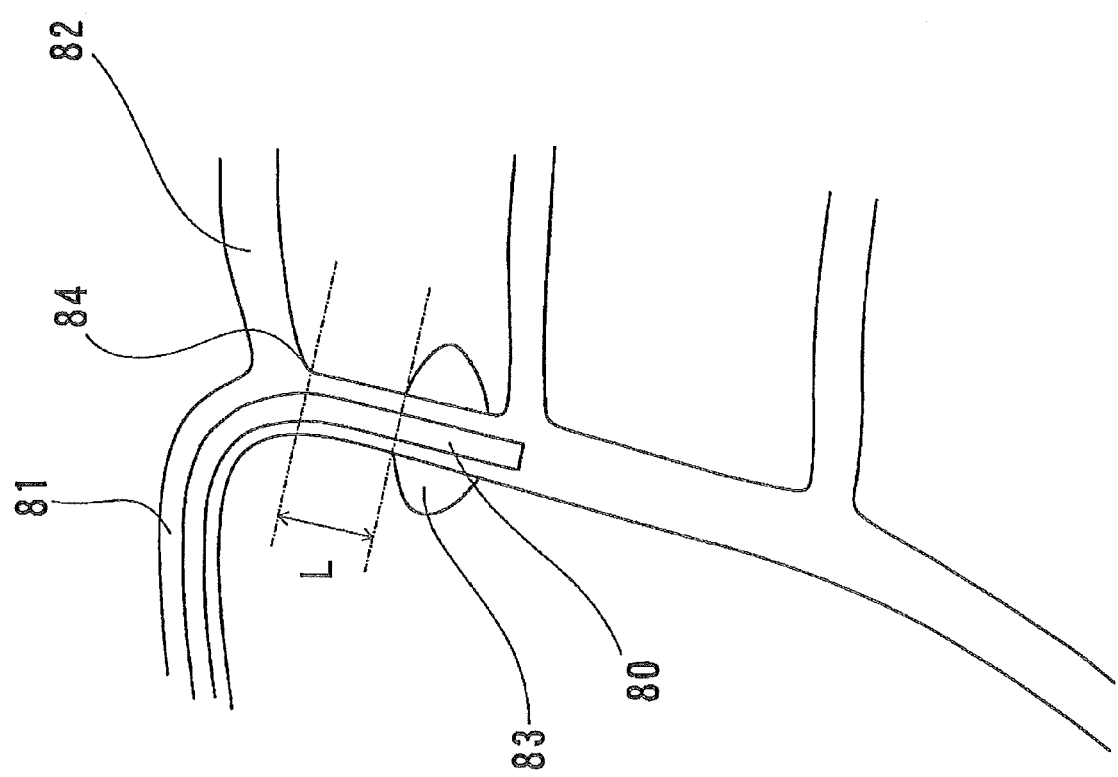
Figure 22:
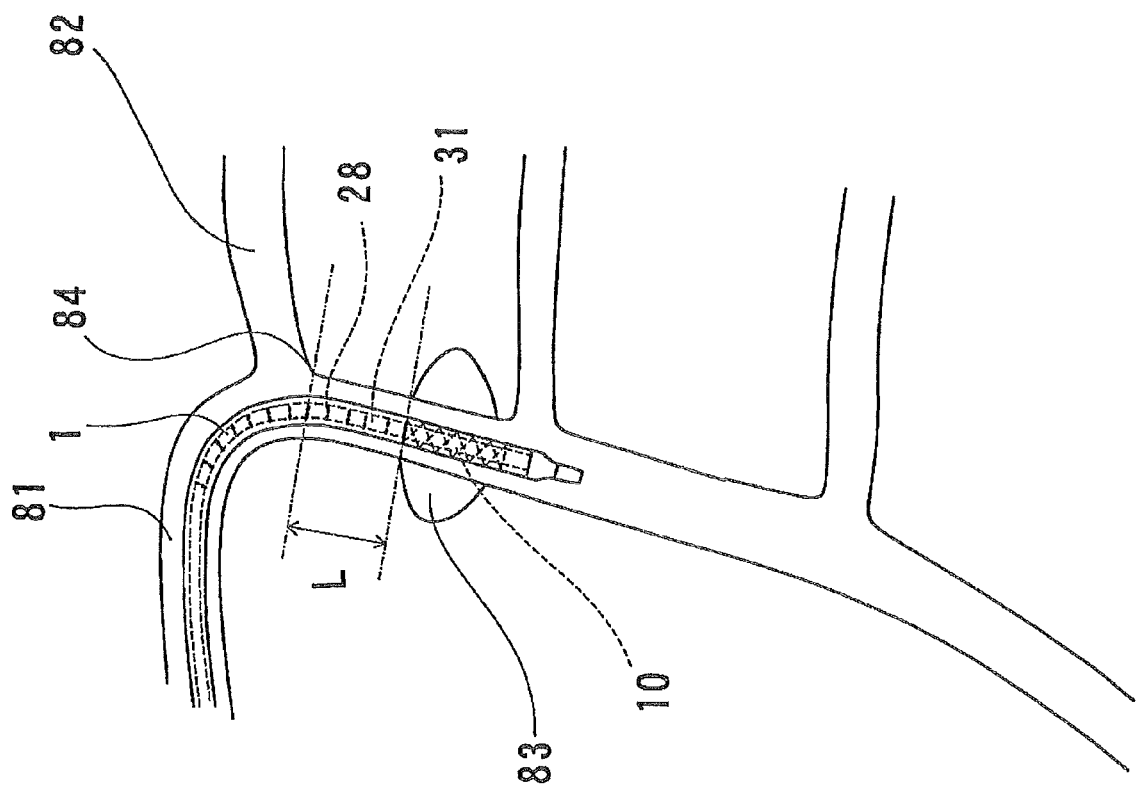

Now, operation of the stent delivery system disclosed here is described below referring to FIGS. 11 and 18-22. Before insertion of the delivery system 1 into a blood vessel, as shown in FIG. 21, a catheter 80 of an OCT system is inserted into the target blood vessel 81, and the distance L between a proximal end of the lesion (plaque) 83 and a bifurcated blood vessel 84 of a branch blood vessel 82 which is on the proximal side in the insertion direction of the delivery system relative to the proximal end of the lesion and the nearest to the proximal end of the lesion is measured by use of the OCT. Then, the catheter 80 of the OCT system is pulled out. Thereafter, as shown in FIG. 22, the delivery system 1 according to the embodiment disclosed here is inserted into the target blood vessel 81, and radiography is conducted. While viewing the radiopaque markers 28 constituting the distance indicating function provided on the distal-side tube 31 of the delivery system 1, the stent 10 of the delivery system 1 inserted into the blood vessel is positioned so that the proximal end of the stent 10 is located on the distal side (on the distal side in the inserting direction of the delivery system) relative to the bifurcated blood vessel 84 by the distance L.

In addition, the indicator for insertion of the delivery system 1 according to the embodiment disclosed here is not limited to the above-mentioned bifurcated blood vessel. By way of example, a stent previously indwelled in the blood vessel, a calcified lesion, other stenosed lesion, a coronary artery inlet or the like may also be used as the indicator. In this case, the catheter of the OCT system is inserted into the target blood vessel, and, while using the OCT, the distance L between the proximal end of the lesion (plaque) and the indicator on the proximal side in the insertion direction of the delivery system relative to the proximal end of the lesion is measured. Then, the catheter of the OCT system is pulled out, the delivery system 1 is inserted into the target blood vessel 81, radiography is conducted. Then, while viewing the radiopaque markers 28 constituting the distance indicating function provided on the distal-side tube 31 of the shaft body 3, the stent 10 of the delivery system 1 is so disposed that the proximal end of the stent 10 is located on the distal side in the insertion direction of the delivery system relative to the indicator by the distance L.

Figure 18:
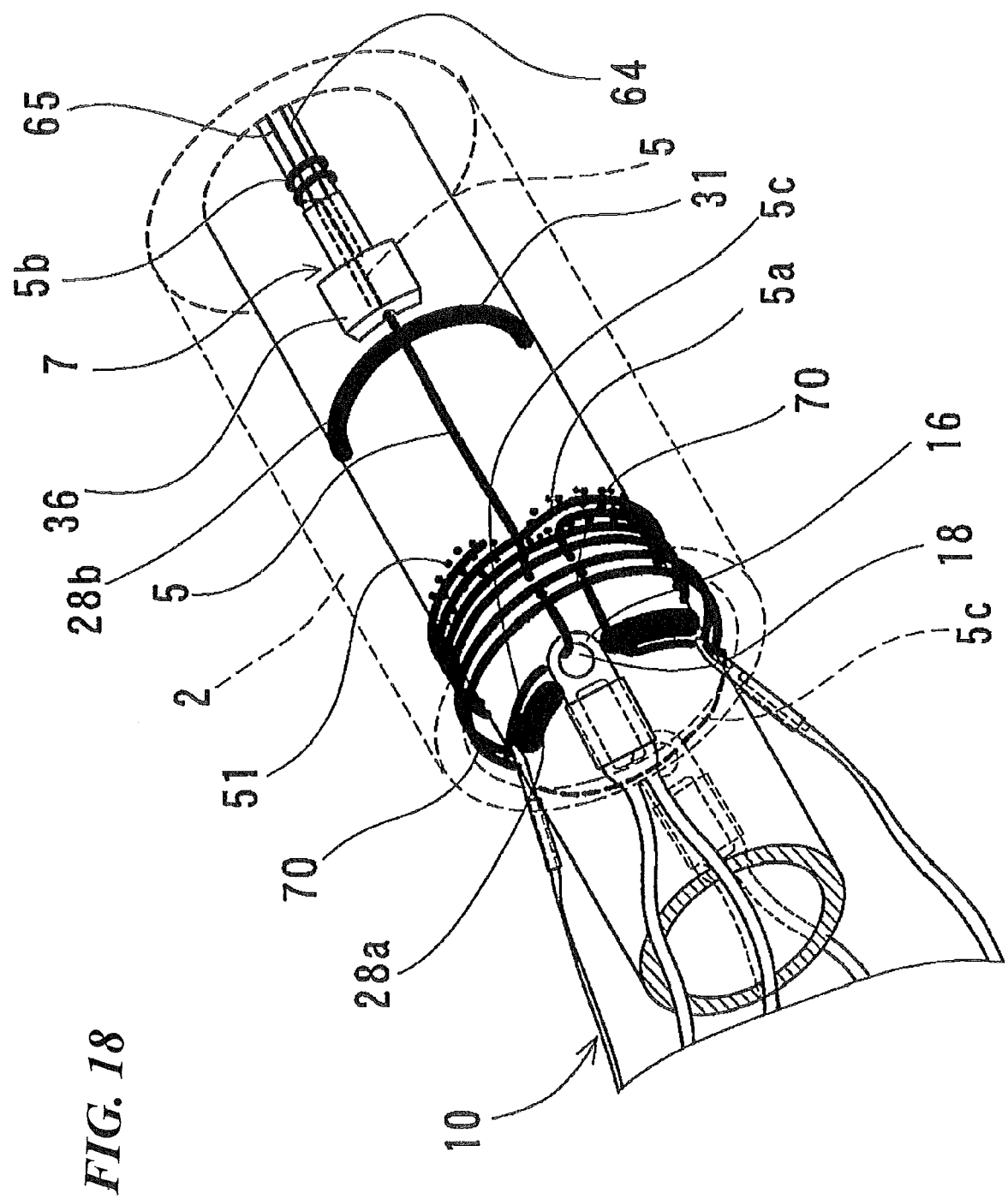
FIGS. 18-22 are explanatory drawings illustrating operation of the delivery system disclosed here.

In the just-mentioned condition, the stent 10 is wholly accommodated in the sheath 2. Then, the sheath 2 is slid toward the proximal side, whereby the stent 10 is exposed from the distal opening of the sheath 2, as shown in FIG. 18. The stent 10 thus exposed from the sheath 2 tends to expand by its self-expanding force to restore its pre-compression shape. In this delivery system 1, however, the proximal end of the stent 10 is moored to the shaft part 3 by the heat-rupturing stent proximal end fixing linear member 5, so that the stent 10 cannot expand, and is in the state shown in FIG. 18. In the case where the position of the stent 10 must be readjusted, the stent 10 can be again accommodated into the sheath 2 by sliding the sheath 2 in the distal direction. Then, after the stent 10 is confirmed to be disposed at the target lesion, the power supply connected to the shaft part 3 is operated to cause the rupture heat generating part 36 to generate heat, whereby the stent proximal end fixing linear member 5 is ruptured or breaks. As a result, the proximal end of the stent 10 is released from the mooring or fixation by the heat-rupturing stent proximal end fixing linear member 5, so that the proximal end also expands, as shown in FIG. 19. Thereafter, the delivery system 1 (the sheath 2 and the shaft part 3) from which the stent 10 has been released is moved in the proximal direction, whereby the intermediate portion 5c of the stent proximal end fixing linear member 5 is disconnected from the stent 10, as shown in FIG. 20. The broken or ruptured stent proximal end fixing linear member 5 inclusive of the intermediate portion 5c is not discharged in vivo or left indwelling near the stent 10, since its one end is fixed to the shaft part 3.

The detailed description above describes a preferred embodiment and variations of the stent delivery system. However it is to be understood that the invention is not limited to the precise embodiment and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent delivery system comprising:
a stent accommodating tube possessing a distal end portion;
an inner tube positioned inside the stent accommodating tube in a manner permitting the stent accommodating tube to be moved proximally relative to the inner tube, the inner tube possessing a guide wire lumen extending along at least a portion of a longitudinal extent of the inner tube and being configured to receive a guide wire, the guide wire lumen having opposite ends opening outside the stent accommodating tube;
a hollow cylindrically shaped stent which possesses a proximal end, the stent being removably positioned in the stent accommodating tube in a configuration in which the stent is inwardly compressed, the stent encircling a distal end portion of the inner tube, the stent being exposable outside the stent accommodating tube by proximally moving the stent accommodating tube relative to the inner tube, the stent being configured to automatically expand outwardly after being exposed outside the stent accommodating tube and left indwelling in vivo;
a plurality of radiopaque markers on the inner tube, the radiopaque markers being spaced apart from one another along a longitudinal extent of the inner tube, the plurality of radiopaque markers comprising a first one of the radiopaque markers positioned at the proximal end of the stent and additional ones of the plurality of radiopaque markers being positioned proximally from the first radiopaque markers, the first radiopaque marker being a distal-most radiopaque marker on the inner tube, adjacent ones of the plurality of radiopaque markers being spaced apart from one another by a common distance to permit distance determination during use of the stent delivery system; and
the radiopaque markers comprising a plurality of main scales and a plurality of auxiliary scales, a plurality of the auxiliary scales being positioned between adjacent ones of the main scales, and the auxiliary scales being lower in radiopacity than the main scales.

2. A stent delivery system comprising:
a stent accommodating tube possessing a distal end portion;
an inner tube positioned inside the stent accommodating tube, the inner tube possessing a guide wire lumen extending along at least a portion of a longitudinal extent of the inner tube and being configured to receive a guide wire;
a stent possessing a hollow cylindrical shape and having a central axis, the stent possessing a proximal end, the stent being removably positioned in the stent accommodating tube and covering a distal end portion of the inner tube, the stent being exposable outside the stent accommodating tube by moving the stent accommodating tube toward the proximal side relative to the inner tube, the stent being configured to be compressed toward its central axis when positioned in the stent accommodating tube and to outwardly expand towards its pre-compression shape after being exposed outside the stent accommodating tube and left indwelling in vivo;
the inner tube comprising a radiopaque indication region extending at least over a predetermined length of the inner tube in a proximal direction from the proximal end of the stent, the radiopaque region comprising a plurality of radiopaque markers, with a distance between adjacent radiopaque markers being the same to permit distance determination; and
the plurality of radiopaque markers are scale-forming radiopaque markers comprising a plurality of main scales and a plurality of auxiliary scales, a plurality of the auxiliary scales being positioned between adjacent ones of the main scales, and the auxiliary scales being lower in radiopacity than the main scales.

3. The stent delivery system according to claim 2, wherein the radiopaque indication region extends proximally over a distance of more than 5 mm from the proximal end of the stent.

4. The stent delivery system according to claim 2, wherein the radiopaque indication region includes a starting point at which is located a first one of the radiopaque markers, the starting point being located at a position corresponding to the distal end or a middle portion of the stent, and the radiopaque indication region extending proximally from the starting point.

5. The stent delivery system according to claim 4, wherein the inner tube includes a distal-side tube having the guide wire lumen, and an inner tube body having a distal portion fixed to a proximal end of the distal-side tube, and the rupture portion is provided at a distal portion of the inner tube body.

6. The stent delivery system according to claim 4, wherein the stent proximal end fixing linear member is a heat-rupturing stent proximal end fixing linear member, and the rupture portion is a heat-rupturing portion.

7. The stent delivery system according to claim 2, comprising a stent proximal end fixing linear member possessing opposite ends both fixed to the inner tube, the stent proximal end fixing linear member also possessing an intermediate portion moored to the proximal end of the stent, the stent proximal end fixing linear member also comprising a rupturable rupture portion configured to rupture the stent proximal fixing linear member to release the mooring of the stent.

8. The stent delivery system according to claim 7, wherein the stent comprises a plurality of through holes arranged in an annular fashion, and the intermediate portion of the stent proximal end fixing linear member passing through the plurality of holes in an annular fashion.

9. The stent delivery system according to claim 7, wherein the proximal end of the stent includes a plurality of proximal end direction bent portions, and the intermediate portion of the stent proximal end fixing linear member passing through the plurality of proximal end direction bent portions in an annular fashion.

10. The stent delivery system according to claim 2, wherein the inner tube has an opening communicating with the guide wire lumen proximally of the stent accommodating portion of the stent accommodating tube, and the radiopaque indication region extends to the opening.

11. A stent delivery system comprising:
a stent accommodating tube possessing a distal end portion;
an inner tube positioned inside the stent accommodating tube in a manner permitting the stent accommodating tube to be moved proximally relative to the inner tube, the inner tube possessing a guide wire lumen extending along at least a portion of a longitudinal extent of the inner tube and being configured to receive a guide wire, the guide wire lumen having opposite ends opening outside the stent accommodating tube;
a hollow cylindrically shaped stent which possesses a proximal end, the stent being removably positioned in the stent accommodating tube in a configuration in which the stent is inwardly compressed, the stent encircling a distal end portion of the inner tube, the stent being exposable outside the stent accommodating tube by proximally moving the stent accommodating tube relative to the inner tube, the stent being configured to automatically expand outwardly after being exposed outside the stent accommodating tube and left indwelling in vivo;
a plurality of radiopaque markers on the inner tube, the radiopaque markers being spaced apart from one another along a longitudinal extent of the inner tube, the plurality of radiopaque markers comprising a first one of the radiopaque markers positioned at the proximal end of the stent and additional ones of the plurality of radiopaque markers being positioned proximally from the first radiopaque markers, the first radiopaque marker being a distal-most radiopaque marker on the inner tube, adjacent ones of the plurality of radiopaque markers being spaced apart from one another by a common distance to permit distance determination during use of the stent delivery system; and
the radiopaque markers comprising a plurality of main scales and a plurality of auxiliary scales, with the main scales being visually distinguishable and visually different from the auxiliary scales, and a plurality of the auxiliary scales being positioned between two adjacent ones of the main scales.

12. A stent delivery system comprising:
a stent accommodating tube possessing a distal end portion;
an inner tube positioned inside the stent accommodating tube, the inner tube possessing a guide wire lumen extending along at least a portion of a longitudinal extent of the inner tube and being configured to receive a guide wire;
a stent possessing a hollow cylindrical shape and having a central axis, the stent possessing a proximal end, the stent being removably positioned in the stent accommodating tube and covering a distal end portion of the inner tube, the stent being exposable outside the stent accommodating tube by moving the stent accommodating tube toward the proximal side relative to the inner tube, the stent being configured to be compressed toward its central axis when positioned in the stent accommodating tube and to outwardly expand towards its pre-compression shape after being exposed outside the stent accommodating tube and left indwelling in vivo;
the inner tube comprising a radiopaque indication region extending at least over a predetermined length of the inner tube in a proximal direction from the proximal end of the stent, the radiopaque region comprising a plurality of radiopaque markers, with a distance between adjacent radiopaque markers being the same to permit distance determination; and
the plurality of radiopaque markers are scale-forming radiopaque markers comprising a plurality of main scales and a plurality of auxiliary scales, with the main scales being visually distinguishable and visually different from the auxiliary scales, and a plurality of the auxiliary scales being positioned between two adjacent ones of the main scales.

* * * * *